United States Patent [19]

Okuhara et al.

[11] Patent Number: 5,254,562
[45] Date of Patent: * Oct. 19, 1993

[54] TRICYCLO COMPOUNDS, A PROCESS FOR THEIR PRODUCTION AND A PHARMACEUTICAL COMPOSITION CONTAINING THE SAME

[75] Inventors: Masakuni Okuhara; Hirokazu Tanaka; Toshio Goto, all of Sakuramura; Tohru Kino, Tsuchiura; Hiroshi Hatanaka, Sakuramura, all of Japan

[73] Assignee: Fujisawa Pharmaceutical Company, Ltd., Osaka, Japan

[ * ] Notice: The portion of the term of this patent subsequent to May 29, 2007 has been disclaimed.

[21] Appl. No.: 900,487

[22] Filed: Jun. 18, 1992

Related U.S. Application Data

[60] Division of Ser. No. 606,837, Oct. 31, 1990, abandoned, which is a division of Ser. No. 491,205, Mar. 9, 1990, Pat. No. 5,110,811, which is a continuation of Ser. No. 868,749, May 30, 1986, Pat. No. 4,929,611, which is a continuation-in-part of Ser. No. 799,855, Nov. 20, 1985, Pat. No. 4,894,366.

[30] Foreign Application Priority Data

Dec. 3, 1984 [GB] United Kingdom ................ 8430455
Feb. 5, 1985 [GB] United Kingdom ................ 8502869
Apr. 1, 1985 [GB] United Kingdom ................ 8508420

[51] Int. Cl.$^5$ .................. A61K 31/395; C07D 498/16
[52] U.S. Cl. ....................... 514/291; 514/63; 514/411; 540/452; 540/456
[58] Field of Search ............ 540/452, 456; 514/291, 514/411, 63

[56] References Cited

U.S. PATENT DOCUMENTS

| | | | |
|---|---|---|---|
| 4,894,366 | 1/1990 | Okuhara et al. | 540/456 |
| 4,929,611 | 5/1990 | Okuhara et al. | 540/452 |
| 4,956,352 | 9/1990 | Okuhara et al. | 540/456 |

Primary Examiner—Robert T. Bond
Attorney, Agent, or Firm—Oblon, Spivak, McClelland, Maier & Neustadt

[57] ABSTRACT

This invention relates to tricyclo compounds useful for treatment and prevention of resistance by transplantation, graft-versus-host diseases by medulla ossium transplantation, autoimmune diseases, infectious diseases, and the like, which can be represented by the following formula:

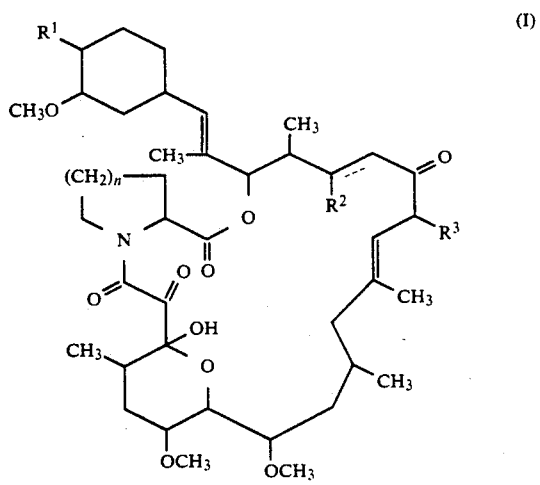

to a process for their production, to a pharmaceutical composition containing the same and to a use thereof.

14 Claims, No Drawings

TRICYCLO COMPOUNDS, A PROCESS FOR THEIR PRODUCTION AND A PHARMACEUTICAL COMPOSITION CONTAINING THE SAME

This is a division of application Ser. No. 07/606,837, filed Oct. 31, 1990, now abandoned; which is a division of application Ser. No. 07/491,205, filed Mar. 9, 1986, now U.S. Pat. No. 4,929,611, which is a continuation in part of application Ser. No. 06/799,855, filed Nov. 20, 1985 now U.S. Pat. No. 4,894,366.

This invention relates to novel tricyclo compounds having pharmacological activities, to a process for their production and to a pharmaceutical composition containing the same.

More particularly, it relates to novel tricyclo compounds, which have pharmacological activities such as immunosuppressive activity, antimicrobial activity, and the like, to a process for their production, to a pharmaceutical composition containing the same and to a use thereof.

Accordingly, one object of this invention is to provide a novel tricyclo compounds, which are useful for treatment and prevention of resistance by transplantation, graft-versus-host diseases by medulla ossium transplantation, autoimmune diseases, infectious diseases, and the like.

Another object of this invention is to provide a process for production of the tricyclo compounds by fermentation processes and synthetic processes.

A further object of this invention is to provide a pharmaceutical composition containing, as active ingredients, the tricyclo compounds.

Still further object of this invention is to provide a use of the tricyclo compounds for manufacturing a medicament for treating and preventing resistance by transplantation, graft-versus-host diseases by medulla ossium transplantation, autoimmune diseases, infectious diseases, and the like.

With respect to the present invention, it is to be noted that this invention is originated from and based on the first and new discovery of new certain specific compounds, FR-900506, FR-900520, FR-900523 and FR-900525 substances In more detail, the FR-900506, FR-900520, FR-900523 and FR-900525 substances were firstly and newly isolated in pure form from culture broths obtained by fermentation of new species belonging to genus Streptomyces.

And, as a result of an extensive study for elucidation of chemical structures of the FR-900506, FR-900520, FR-900523 and FR-900525 substances, the inventors of this invention have succeeded in determining the chemical structures thereof and in producing the tricyclo compounds of this invention.

The new tricyclo compounds of this invention can be represented by the following general formula:

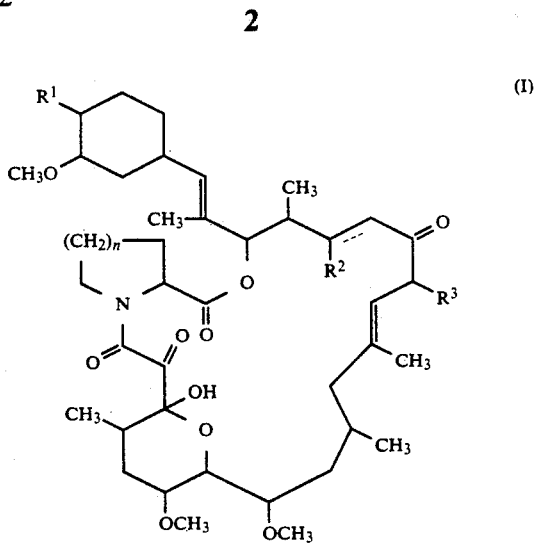

wherein
$R^1$ is hydroxy or protected hydroxy,
$R^2$ is hydrogen, hydroxy or protected hydroxy,
$R^3$ is methyl, ethyl, propyl or allyl,
n is an integer of 1 or 2, and the symbol of a line and dotted line is a single bond or a double bond, and salts thereof.

Among the object compound (I), the following four specific compounds were found to be produced by fermentation.

(1) The compound (I) wherein $R^1$ and $R^2$ are each hydroxy, $R^3$ is allyl, n is an integer of 2, and the symbol of a line and dotted line is a single bond, which is entitled to the FR-900506 substance;

(2) The compound (I) wherein $R^1$ and $R^2$ are each hydroxy, $R^3$ is ethyl, n is an integer of 2, and the symbol of a line and dotted line is a single bond, which is entitled to the FR-900520 substance (another name: the WS 7238A substance);

(3) The compound (I) wherein $R^1$ and $R^2$ are each hydroxy, $R^3$ is methyl, n is an integer of 2, and the symbol of a line and dotted line is a single bond, which is entitled to the FR-900523 substance (another name: the WS 7238B substance); and (4) The compound (I) wherein $R^1$ and $R^2$ are each hydroxy, $R^3$ is allyl, n is an integer of 1, and the symbol of a line and dotted line is a single bond, which is entitled to the FR-900525 substance.

With respect to the tricyclo compounds (I) of this invention, it is to be understood that there may be one or more conformer(s) or stereoisomeric pairs such as optical and geometrical isomers due to asymmetric carbon atom(s) and double bond(s), and such isomers are also included within a scope of this invention.

According to this invention, the object tricyclo compounds (I) can be prepared by the following processes

[I] Fermentation Processes:

Species belonging to the genus Streptomyces →Fermentation→ { FR-900506 substance, FR-900520 substance, FR-900523 substance and FR-900525 substance

[II] Synthetic Processes

(1) Process 1 (Introduction of Hydroxy-Protective Group)

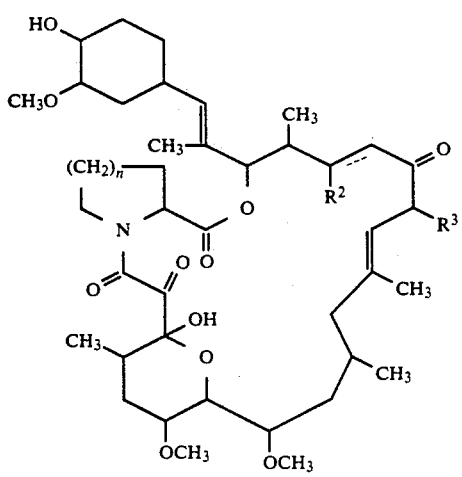

(Ia) or a salt thereof

↓ Introduction of Hydroxy-Protective Group

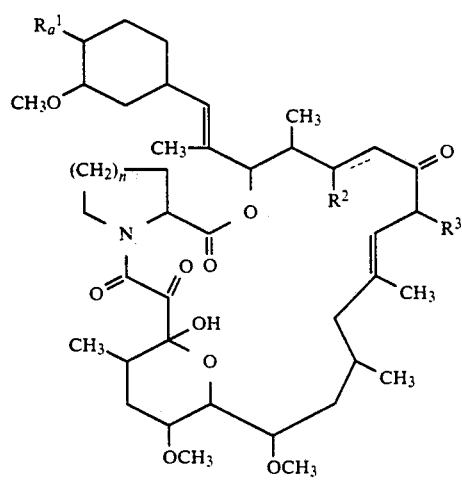

(Ib) or a salt thereof

(2) Process 2 (Introduction of Hydroxy-Protective Group)

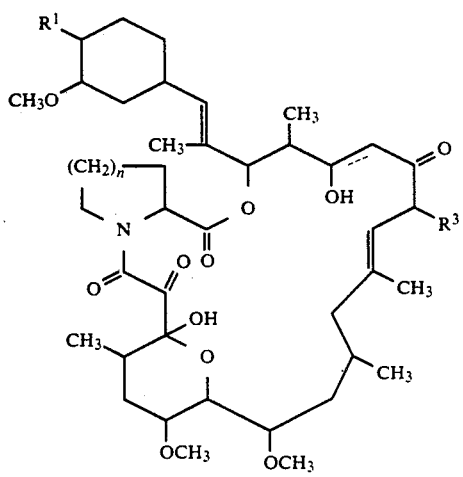

(Ic) or a salt thereof

↓ Introduction of Hydroxy-Protective Group

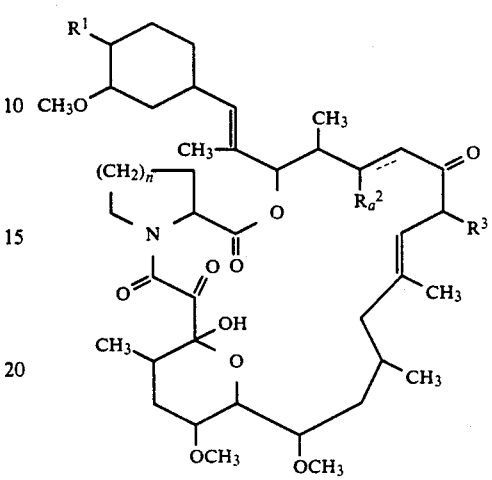

(Id) or a salt thereof

(3) Process 3 (Formation of Double Bond)

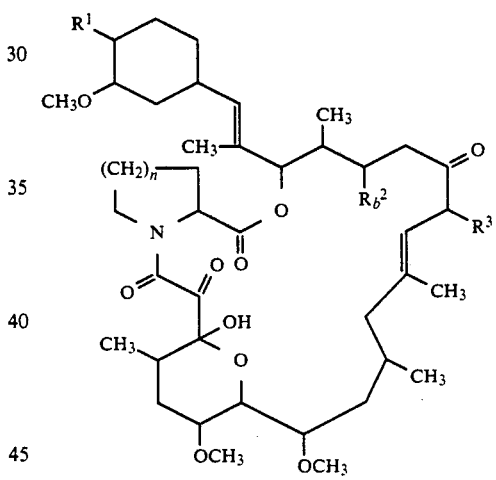

(Ie) or a salt thereof

↓ Base

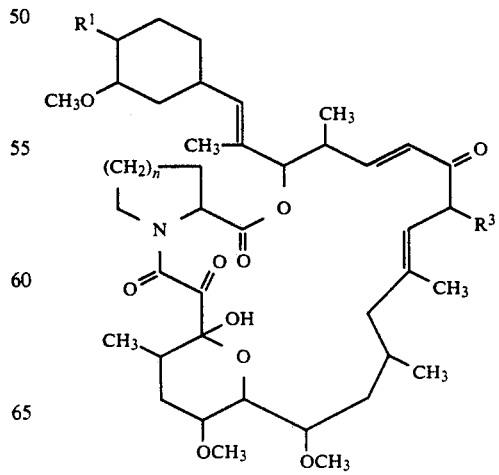

(If) or a salt thereof

(4) Process 4 (Oxidation of Hydroxyethylene Group)

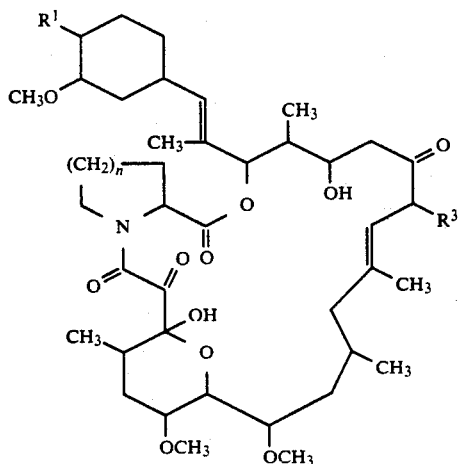
(Ig) or a salt thereof

↓ Oxidation of Hydroxyethylene Group

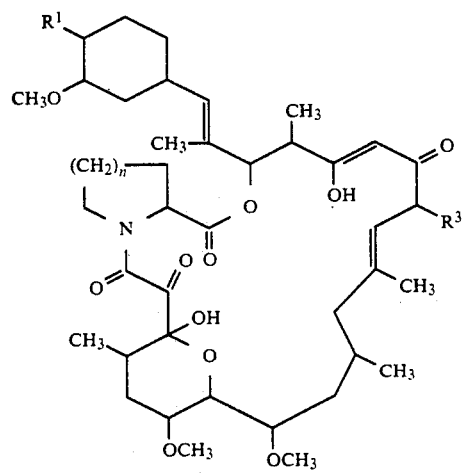
(Ih) or a salt thereof

(5) Process 5 (Reduction of Allyl Group)

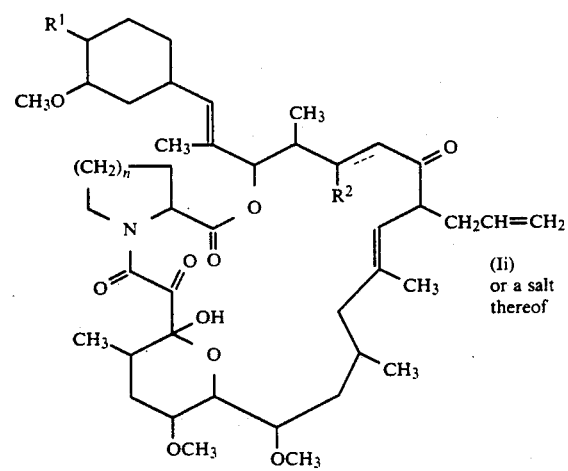
(Ii) or a salt thereof

↓ Reduction

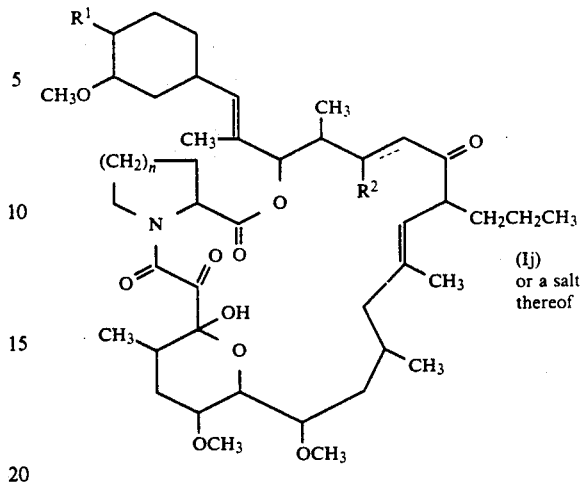
(Ij) or a salt thereof

(6) Process 6 (Removal of the Carboxy-Protective Group)

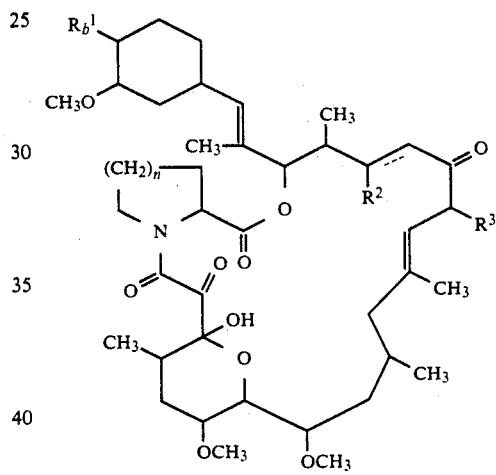
(Ik) or a salt thereof

↓ Removal of the carboxy-protective group

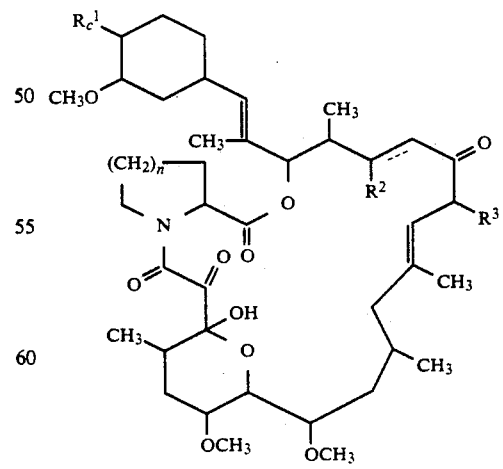
(Il) or a salt thereof in which
$R^1$, $R^2$, $R^3$, n and the symbol of a line and dotted line are each as defined above, $R_a{}^1$ and $R_a{}^2$ are each protected hydroxy, $R_b{}^1$ is protected carboxy(lower)alkyl-carbamoyloxy, $R_c{}^1$ is carboxy(lower)alkylcarbamoyloxy, and $R_b{}^2$ is a leaving group.

Particulars of the above definitions and the preferred embodiments thereof are explained in detail as follows.

The term "lower" used in the specification is intended to mean 1 to 6 carbon atoms, unless otherwise indicated.

Suitable hydroxy-protective group in the "protected hydroxy" may include:

1-(lower alkylthio)(lower)alkyl such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$alkylthiomethyl and the most preferred one may be methylthiomethyl;

trisubstituted silyl such as tri(lower)alkylsilyl (e.g. trimethylsilyl, triethylsilyl, tributylsilyl, tert-butyldimethylsilyl, tri-tert-butylsilyl, etc.), lower alkyldiarylsilyl (e.g. methyl-diphenylsilyl, ethyl-diphenylsilyl, propyl-diphenylsilyl, tert-butyl-diphenylsilyl, etc.), and the like, in which the preferred one may be tri($C_1$-$C_4$)alkylsilyl and $C_1$-$C_4$alkyl-diphenylsilyl, and the most preferred one may be tert-butyl-dimethylsilyl and tert-butyldiphenylsilyl;

acyl such as aliphatic acyl, aromatic acyl and aliphatic acyl substituted with aromatic group, which are derived from carboxylic, sulfonic and carbamic acids; and the like.

The aliphatic acyl may include lower alkanoyl which may have one or more suitable substituent(s) such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkyloxy(lower)alkanoyl which may have one or more suitable substituent(s) such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxyheptanoyl, menthyloxyhexanoyl, etc.), camphorsulfonyl, lower alkylcarbamoyl having one or more suitable substituent(s) such as carboxy and a protected carboxy, for example, carboxy(lower)alkylcarbamoyl (e.g. carboxymethylcarbamoyl, carboxyethylcarbamoyl, carboxypropylcarbamoyl, carboxybutylcarbamoyl, carboxypentylcarbamoyl, carboxyhexylcarbamoyl, etc.), protected carboxy(lower)alkylcarbamoyl such as tri(lower)alkylsilyl(lower)alkoxycarbonyl(lower)alkylcarbamoyl (e.g. trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.), and the like.

The aromatic acyl may include aroyl which may have one or more suitable substituent(s) such as nitro (e.g. benzoyl, toluoyl, xyloyl, naphthoyl, nitrobenzoyl, dinitrobenzoyl, nitronaphthoyl, etc ), arenesulfonyl which may have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc ), and the like.

The aliphatic acyl substituted with aromatic group may include ar(lower)alkanoyl which may have one or more suitable substituent(s) such as lower alkoxy and trihalo(lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.), and the like.

The more preferred acyl group thus defined may be $C_1$-$C_4$alkanoyl which may have carboxy, cyclo($C_5$-$C_6$)-alkyloxy($C_1$-$C_4$)alkanoyl having two ($C_1$-$C_4$)alkyl groups on the cycloalkyl moiety, camphorsulfonyl, carboxy($C_1$-$C_4$)-alkylcarbamoyl, tri($C_1$-$C_4$)alkylsilyl(-$C_1$-$C_4$)alkoxycarbonyl($C_1$-$C_4$)alkylcarbamoyl, benzoyl which may have one or two nitro, benzenesulfonyl having halogen, phenyl($C_1$-$C_4$)alkanoyl having $C_1$-$C_4$alkoxy and trihalo($C_1$-$C_4$)alkyl, and the most preferred one may be acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Suitable "protected carboxy(lower)alkylcarbamoyl" and "carboxy(lower)alkylcarbamoyl" moieties of the "protected carboxy(lower)alkylcarbamoyloxy" and "carboxy(lower)alkyl-carbamoyloxy" groups may include the same as those exemplified in the explanation of the hydroxy-protective group mentioned above.

Suitable "leaving group" may include hydroxy, acyloxy in which the acyl moiety may be those as exemplified above, and the like.

The processes for production of the tricyclo compounds (I) of this invention are explained in detail in the following.

[I] Fermentation Processes

The FR-900506, FR-900520, FR-900523 and FR-900525 substances of this invention can be produced by fermentation of FR-900506, FR-900520, FR-900523 and/or FR-900525 substance(s)-producing strains belonging to the genus Streptomyces such as *Streptomyces tsukubaensis* No. 9993 and *Streptomyces hygroscopicus* subsp. yakushimaensis No. 7238 in a nutrient medium.

Particulars of microorganisms used for the production of the FR-900506, FR-900520, FR-900523 and FR-900525 substances are explained in the following.

[A] The FR-900506, FR-900520 and FR-900525 substances of this invention can be produced by fermentation of a FR-900506, FR-900520 and/or FR-900525 substance(s)-producing strain belonging to the genus Streptomyces such as *Streptomyces tsukubaensis* No. 9993 in a nutrient medium.

THE MICROORGANISM

The microorganism which can be used for the production of the FR-900506, FR-900520 and/or FR-900525 substances is FR-900506, FR-900520 and/or FR-900525 substance(s)-producing strain belonging to the genus Streptomyces, among which *Streptomyces tsukubaensis* No. 9993 has been newly isolated from a soil sample collected at Toyosato-cho, Tsukuba-gun, Ibaraki Prefecture, Japan.

A lyophilized sample of the newly isolated *Streptomyces tsukubaensis* No. 9993 has been deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposited date: Oct. 5, 1984), and then converted to Budapest Treaty route of the same depository on Oct. 19, 1985 under the new deposit number of FERM BP-927.

It is to be understood that the production of the novel FR-900506, FR-900520 and/or FR-900525 substance(s) is not limited to the use of the particular organism described herein, which is given for the illustrative purpose only. This invention also includes the use of any mutants which are capable of producing the FR-900506, FR-900520 and/or FR-900525 substances including natural mutants as well as artificial mutants which can be produced from the described organism by conventional means such as irradiation of X-rays, ultra-violet radiation, treatment with N-methyl-N'-nitro-N-nitrosoguanidine, 2-aminopurine, and the like.

The *Streptomyces tsukubaensis* No. 9993 has the following morphological, cultural, biological and physiological characteristics.

[1] Morphological Characteristics:

The methods described by Shirling and Gottlieb (Shirling, E. B. and D. Gottlieb: Methods for characterization of Streptomyces species International Journal of Systematic Bacteriology, 16, 313-340, 1966) were employed principally for this taxonomic study.

Morphological observations were made with light and electron microscopes on cultures grown at 30° C. for 14 days on oatmeal agar, yeast-malt extract agar and inorganic salts-starch agar. The mature sporophores formed Rectiflexibiles with 10 to 50 or more than 50 spores in each chain. The spores were oblong or cylindrical, 0.5–0.7×0.7–0.8 μm in size by electron microscopic observation. Spore surfaces were smooth.

[2] Cultural Characteristics:

Cultural characteristics were observed on ten kinds of media described by Shirling and Gottlieb as mentioned above, and by Waksman (Waksman, S. A.: The actinomycetes, vol. 2: Classification, identification and description of genera and species. The Williams and Wilkins Co., Baltimore, 1961).

The incubation was made at 30° C. for 14 days. The color names used in this study were based on Guide to Color Standard (manual published by Nippon Shikisai Kenkyusho, Tokyo). Colonies belonged to the gray color series when grown on oatmeal agar, yeast-malt extract agar and inorganic salts-starch agar. Soluble pigment was produced in yeast-malt extract agar but not in other media. The results are shown in Table 1.

TABLE 1

Cultural Characteristics of Strain No. 9993 and *Streptomyces misakiensis* IFO 12891

| Medium | | No. 9993 | IFO 12891 |
|---|---|---|---|
| Oatmeal Agar | G | Moderate | Moderate |
| | A | Gray | Grayish White |
| | R | Pale Pink | Colorless |
| | S | None | None |
| Yeast-Malt | G | Moderate | Moderate |
| Extract Agar | A | Light Gray | Grayish White |
| | R | Dull Reddish Orange | Light Brown |
| | S | Dull Reddish Orange | None |
| Inorganic Salts- | G | Moderate | Moderate |
| Starch Agar | A | Pale Yellow Orange to Light Gray | Grayish White |
| | R | Dark Orange | Pale Yellowish Brown |
| | S | None | None |
| Glucose- | G | Poor | Moderate |
| Asparagine | A | White | Grayish White |
| Agar | R | Pale Brown | Pale Yellowish Brown |
| | S | None | Pale Brown |
| Glycerin- | G | Moderate | Moderate |
| Asparagine | A | Pale Pink to White | Grayish White |
| Agar | R | Pale Pink | Pale Yellowish Brown |
| | S | None | Pale Brown |
| Czapek Agar | G | Poor | Abundant |
| | A | None | Grayish White |
| | R | Pale Pink | Dark Orange to Dark Brown |
| | S | None | None |
| Nutrient Agar | G | Poor | Poor |
| | A | White, Poor | White |
| | R | Colorless | Colorless |
| | S | None | None |
| Potato-Dextrose | G | Poor | Moderate |
| Agar | A | None | Yellowish Gray |
| | R | Pale Pink | Brown |
| | S | None | None |
| Tyrosine Agar | G | Moderate | Moderate |
| | A | White | Grayish White to Light Gray |
| | R | Dull Reddish Orange | Dark Orange to Black |
| | S | None | None |
| Peptone-Yeast | G | Poor | Poor |
| Extract-Iron | A | None | None |
| Agar | R | Colorless | Colorless |
| | S | None | None |

Abbreviation:
G = Growth,
A = Aerial Mass Color,
R = Reverse Side Color,
S = Soluble Pigment, The cell wall analysis was performed by the methods of Becker et al. (Becker, B., M. P. Lechevalier, R. E. Gordon and H. A. Lechevalier: Rapid differentiation between Nocardia and Streptomyces by paper chromatography of whole cell hydrolysates: Appl. Microbiol., 12, 421-423, 1964) and Yamaguchi (Yamaguchi, T.: Comparison of the cell wall composition of morphologically distinct actinomycetes: J. Bacteriol., 89, 444-453, 1965). Analysis of whole cell hydrolysates of the strain No. 9993 showed the presence of LL-diaminopimelic acid. Accordingly, the cell wall of this strain is believed to be of type I.

[3] Biological and Physiological Properties:

Physiological properties of the strain No. 9993 were determined according to the methods described by Shirling and Gottlieb as mentioned above. The results are shown in Table 2. Temperature range and optimum temperature for growth were determined on yeast-malt extract agar using a temperature gradient incubator (made by Toyo Kagaku Sangyo Co., Ltd.). Temperature range for growth was from 18° to 35° C. with optimum temperature at 28° C. Milk peptonization and gelatin liquefaction were positive Melanoid pigment production was negative.

TABLE 2

Physiological Properties of Strain No. 9993 and *Streptomyces misakiensis* IFO 12891

| Physiological properties | No. 9993 | IFO 12891 |
| --- | --- | --- |
| Temperature Range for Growth | 18° C.-35° C. | 12° C.-35° C. |
| Optimum Temperature | 28° C. | 28° C. |
| Nitrate Reduction | Negative | Negative |
| Starch Hydrolysis | Negative | Positive |
| Milk Coagulation | Negative | Negative |
| Milk Peptonization | Positive | Weakly Positive |
| Melanin Production | Negative | Negative |
| Gelatin Liquefaction | Positive | Negative |
| H$_2$S Production | Negative | Negative |
| NaCl Tolerance (%) | ≦3% | 3% <. <5% |

Utilization of carbon sources was examined according to the methods of Pridham and Gottlieb (Pridham, T. G. and D. Gotlieb: The utilization of carbon compounds by some Actinomycetales as an aid for species determination: J. Bacteriol., 56, 107-114, 1948). The growth was observed after 14 days incubation at 30° C.

Summarized carbon sources utilization of this strain is shown in Table 3. Glycerin, maltose and sodium succinate could be utilized by the strain No 9993. Further, doubtful utilization of D-glucose, sucrose, D-mannose and salicin was also observed.

TABLE 3

Carbon Sources Utilization of Strain No. 9993 and *Streptomyces misakiensis* IFO 12891

| Carbon Sources | No. 9993 | IFO 12891 |
| --- | --- | --- |
| D-Glucose | ± | − |
| Sucrose | ± | − |
| Glycerin | + | − |
| D-Xylose | − | − |
| D-Fructose | − | − |
| Lactose | − | − |
| Maltose | + | − |
| Rhamnose | − | − |
| Raffinose | − | − |
| D-Galactose | − | + |
| L-Arabinose | − | − |
| D-Mannose | ± | − |
| D-Trehalose | − | − |
| Inositol | − | − |
| D-Mannitol | − | − |
| Inulin | − | + |
| Cellulose | − | − |
| Salicin | ± | − |
| Chitin | − | ± |
| Sodium Citrate | − | − |
| Sodium Succinate | + | − |

TABLE 3-continued

Carbon Sources Utilization of Strain No. 9993 and *Streptomyces misakiensis* IFO 12891

| Carbon Sources | No. 9993 | IFO 12891 |
| --- | --- | --- |
| Sodium Acetate | − | − |

Symbols:
+: utilization
±: doubtful utilization
−: no utilization

Microscopic studies and cell wall composition analysis of the strain No. 9993 indicate that this strain belongs to the genus Streptomyces Waksman and Henrici 1943.

Accordingly, a comparison of this strain was made with various Streptomyces species in the light of the published descriptions [International Journal of Systematic Bacteriology, 18, 69 to 189, 279 to 392 (1968) and 19, 391 to 512 (1969), and Bergy's Manual of Determinative Bacteriology 8th Edition (1974)].

As a result of the comparison, the strain No. 9993 is considered to resemble *Streptomyces aburaviensis* Nishimura et. al., *Streptomyces avellaneus* Baldacci and Grein and *Streptomyces misakiensis* Nakamura Therefore, the cultural characteristics of the strain No. 9993 were compared with the corresponding *Streptomyces aburaviensis* IFO 12830, *Streptomyces avellaneus* IFO 13451 and *Streptomyces misakiensis* IFO 12891 As a result, the strain No. 9993 was the most similar to *Streptomyces misakiensis* IFO 12891 Therefore, the strain No. 9993 was further compared with *Streptomyces misakiensis* IFO 12891 as shown in the above Tables 1, 2 and 3. From further comparison, the strain No. 9993 could be differentiated from *Streptomyces misakiensis* IFO 12891 in the following points, and therefore the strain No. 9993 is considered to be a new species of Streptomyces and has been designated as *Streptomyces tsukubaensis* sp. nov., referring to the soil collected at Tsukuba-gun, from which the organism was isolated.

Difference from *Streptomyces misakiensis* IFO 12891

Cultural characteristics of the strain No. 9993 are different from the *Streptomyces misakiensis* IFO 12891 on oatmeal agar, yeast-malt extract agar, glucose-asparagine agar, Czapek agar and potato-dextrose agar.

Starch hydrolysis of the strain No. 9993 is negative, but that of the *Streptomyces misakiensis* IFO 12891 is positive.

Gelatin liquefaction of the strain No. 9993 is positive, but that of the *Streptomyces misakiensis* IFO 12891 is negative.

In carbon sources utilization, the strain No. 9993 can utilize glycerin, maltose and sodium succinate, but the *Streptomyces misakiensis* IFO 12891 can not utilize them. And, the strain No. 9993 can not utilize D-galactose and inulin, but the *Streptomyces misakiensis* IFO 12891 can utilize them.

PRODUCTION OF FR-900506, FR-900520 AND FR-900525 SUBSTANCES

The novel FR-900506, FR-900520 and FR-900525 substances of this invention can be produced by culturing a FR-900506, FR-900520 and/or FR-900525 substance(s)-producing strain belonging to the genus Streptomyces (e.g. *Streptomyces tsukubaensis* No. 9993, FERM BP-927) in a nutrient medium.

In general, the FR-900506, FR-900520 and/or FR-900525 substance(s) can be produced by culturing the FR-900506, FR-900520 and/or FR-900525 substance(s)- producing strain in an aqueous nutrient medium containing sources of assimilable carbon and nitrogen, preferably under aerobic conditions (e.g. shaking culture, submerged culture, etc.).

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, peptone, gluten meal, cottonseed meal, soybean meal, corn steep liquor, dried yeast, wheat germ, feather meal, peanut powder etc., as well as inorganic and organic nitrogen compounds such as ammonium salts (e.g. ammonium nitrate, ammonium sulfate, ammonium phosphate, etc.), urea, amino acid, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salt and the like. If necessary, especially when the culture medium foams seriously, a defoaming agent, such as liquid paraffin, fatty oil, plant oil, mineral oil or silicone may be added.

As the conditions for the production of the FR-900506, FR-900520 and FR-900525 substances in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-900506, FR-900520 and FR-900525 substances. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of the FR-900506, FR-900520 and FR-900525 substances.

Agitation and aeration of the culture mixture may be accomplished in a variety of ways Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 50 hours to 150 hours, which may be varied according to fermentation conditions and scales.

Thus produced FR-900506, FR-900520 and/or FR-900525 substance(s) can be recovered from the culture medium by conventional means which are commonly used for the recovery of other known biologically active substances. The FR-900506, FR-900520 and FR-900525 substances produced are found in the cultured mycelium and filtrate, and accordingly the FR-900506, FR-900520 and FR-900525 substances can be isolated and purified from the mycelium and the filtrate, which are obtained by filtering or centrifuging the cultured broth, by a conventional method such as concentration under reduced pressure, lyophilization, extraction with a conventional solvent, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like.

PHYSICAL AND CHEMICAL PROPERTIES OF FR-900506, FR-900520 AND FR-900525 SUBSTANCES

The FR-900506, FR-900520 and FR-900525 substances produced according to the aforementioned process possess the following physical and chemical properties.

FR-900506 Substance (1) Form and Color:
white powder (2) Elemental Analysis: C: 64.72%; H: 8.78%; N: 1.59%; 64.59%; 8.74%; 1.62%.

(3) Color Reaction:
Positive cerium sulfate reaction, sulfuric acid reaction, Ehrlich reaction, Dragendorff reaction and iodine vapor reaction
Negative: ferric chloride reaction, ninhydrin reaction and Molish reaction (4) Solubility:
Soluble: methanol, ethanol, acetone, ethyl acetate, chloroform, diethyl ether and benzene
Sparingly Soluble: hexane, petroleum ether
Insoluble: water (5) Melting Point:
85°-90 ° C.

(6) Specific Rotation: $[\alpha]_D^{23} -73°$ (c=0.8, CHCl$_3$)

(7) Ultraviolet Absorption Spectrum
end absorption (8) Infrared Absorption Spectrum:
CHCl$_3$γmax: 3680, 3580, 3520, 2930, 2870, 2830, 1745, 1720, 1700, 1645, 1450, 1380, 1350, 1330, 1310, 1285, 1170, 1135, 1090, 1050, 1030, 1000, 990, 960(sh), 918 cm$^{-1}$ (9) $^{13}$C Nuclear Magnetic Resonance Spectrum

| δ (ppm, CDCl$_3$): | | | |
|---|---|---|---|
| 212.59 (s), 212.45 (s), | 196.18 (s) 192.87 (s), | 169.07 (s) 168.90 (s), |
| 164.90 (s) 166.01 (s), | 138.89 (s) 139.67 (s), | 135.73 (d) 135.60 (d), |
| 132.52 (s) 131.99 (s), | 130.27 (d) 130.21 (d), | 122.87 (d) 123.01 (d), |
| 116.57 (t) 116.56 (t), | 97.35 (s) 98.76 (s), | 84.41 (d), |
| 77.79 (d) 78.22 (d), | 75.54 (d) 76.97 (d), | 73.93 (d) 73.09 (d), |
| 73.72 (d) 72.57 (d), | 70.05 (d) 69.15 (d), | 56.75 (d), |
| 53.03 (d) 53.13 (d), | 48.85 (t) 48.62 (t), | 40.33 (d) 40.85 (d), |
| 39.40 (t), | | |
| 31.58 (t), | 30.79 (t), | 27.72 (t) |

-continued

| | | 26.34 (t), |
|---|---|---|
| 26.46 (d), | 24.65 (t), | 20.45 (q) |
| | | 19.73 (q), |
| 14.06 (q) | 9.69 (q) | |
| 14.23 (q), | 9.98 (q), | | the chart of which being shown in FIG. 1,

(10) $^1$H Nuclear Magnetic Resonance Spectrum: the chart of which being shown in FIG. 2,

(11) Thin Layer Chromatography:

| Stationary Phase | Developing Solvent | Rf Values |
|---|---|---|
| silica gel plate | chloroform :methanol (10:1, v/v) | 0.58 |
| | ethyl acetate | 0.52 |

(12) Property of the Substance: nuetral substance

With regard to the FR-900506 substance, it is to be noted that in case of measurements of $^{13}$C and $^1$H nuclear magnetic resonance spectra, this substance showed pairs of the signals in various chemical shifts.

The FR-900506 substance thus characterized further possesses the following properties.

(i) The measurements of $^{13}$C Nuclear Magnetic Resonance Spectra at 25° C. and 60° C. revealed the fact that the intensities of each pair of the various signals therein were changed.

(ii) The measurements of the thin layer chromatography and the high performance liquid chromatography revealed that the FR-900506 substance occurs as a single spot in the thin layer chromatography and a single peak in the high performance liquid chromatography, respectively.

This white powder of the FR-900506 substance could be transformed into a form of crystals by recrystallization thereof from acetonitrile, which possess the following physical and chemical properties.

(1) Form and Color:
colorless prisms (2) Elemental Analysis:
C: 64.30%; H: 8.92%; N:1.77%; 64.20%; 8.86%; 1.72%.

(3) Melting Point:
127°–129° C.

(4) Specific Rotation:
$[\alpha]_D^{23}$: −84.4° (c=1.02, CHCl$_3$)

(5) $^{13}$C Nuclear Magnetic Resonance Spectrum:

| δ (ppm, CDCl$_3$): | 211.98 (s) | 196.28 (s) | 168.97 (s) |
|---|---|---|---|
| | 211.74 (s), | 193.56 (s), | 168.81 (s), |
| | 164.85 (s) | 138.76 (s) | 135.73 (d) |
| | 165.97 (s), | 139.51 (s), | 135.63 (d), |
| | 132.38 (s) | 130.39 (d) | 122.82 (d) |
| | 131.90 (s), | 130.17 (d), | 122.96 (d), |
| | 116.43 (t), | 97.19 (s) | 84.29 (d). |
| | | 98.63 (s). | |
| | 77.84 (d) | 77.52 (d) | 69.89 (d) |
| | 78.21 (d), | 76.97 (d), | 69.00 (d), |
| | 56.63 (d) | 52.97 (d) | 48.76 (t) |
| | 54.87 (d), | 52.82 (d), | 48.31 (t). |
| | 40.21 (d) | 31.62 (t), | 30.72 (t). |
| | 40.54 (d), | | |
| | 24.56 (t), | 21.12 (t) | 20.33 (q) |
| | | 20.86 (t), | 19.74 (q), |
| | 16.17 (q) | 15.88 (q) | 13.89 (q) |
| | 16.10 (q), | 15.75 (q). | 14.05 (q), |
| | 9.64 (q) | | |
| | 9.96 (q), | | | the chart of which being shown in FIG. 3, (6) $^1$H Nuclear Magnetic Resonance Spectrum: the chart of which being shown in FIG. 4.

Other physical and chemical properties, that is, the color reaction, solubility, ultraviolet absorption spectrum, infrared absorption spectrum, thin layer chromatography and property of the substance of the colorless prisms of the FR-900506 substance were the same as those for the white powder of the same under the identical conditions. From the above physical and chemical properties and the analysis of the X ray diffraction, the FR-900506 substance could be determined to have the following chemical structure.

17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone FR-900520 Substance The physical and chemical properties are mentioned later.

FR-900525 Substance (1) Form and Color:
white powder (2) Elemental Analysis: C: 65.17%; H: 8.53%; N: 1.76%.

(3) Color Reaction:
Positive: cerium sulfate reaction, sulfuric acid reaction, Ehrlich reaction, Dragendorff reaction and iodine vapor reaction Negative: ferric chloride reaction, ninhydrin reaction and Molish reaction (4) Solubility:
Soluble: methanol, ethanol, acetone, ethyl acetate, chloroform, diethyl ether and benzene Sparingly Soluble: hexane, petroleum ether
Insoluble: water (5) Melting Point:
85°-89° C.

(6) Specific Rotation:
$[\alpha]_D^{23}: -88+$ (c=1.0 CHCl$_3$)

(7) Ultraviolet Absorption Spectrum:
end absorption (8) Infrared Absorption Spectrum:
CHCl$_3$γmax: 3680, 3580, 3475, 3340, 2940, 2880, 2830, 1755, 1705, 1635, 1455, 1382, 1370, 1330, 1310, 1273, 1170, 1135, 1093, 1050, 1020, 995, 970, 920, 867 cm$^{-1}$ (9) $^{13}$C Nuclear Magnetic Resonance Spectrum:

| δ (ppm, CDCl$_3$): | | | |
|---|---|---|---|
| 212.61 (s) | 188.57 (s) | 168.76 (s) | |
| 211.87 (s), | 191.12 (s), | 170.18 (s), | |
| 163.11 (s) | 140.28 (s) | 135.62 (d) | |
| 161.39 (s), | 139.37 (s), | 135.70 (d), | |
| 132.28 (s) | 130.09 (d) | 122.50 (d) | |
| 131.34 (s), | 130.00 (d), | 123.23 (d), | |
| 116.48 (t), | 99.16 (s) | 84.42 (d) | |
| | 99.11 (s), | 84.48 (d), | |
| 78.60 (d) | 76.73 (d) | 59.97 (d) | |
| 79.86 (d), | 77.33 (d), | 60.45 (d), | |
| 57.52 (q), | 56.56 (q) | 56.14 (q) | |
| | 56.48 (q), | 55.97 (q), | |
| 53.45 (d) | 49.15 (t) | 48.46 (t) | |
| 53.26 (d), | 49.73 (t), | 47.62 (t), | |
| 44.47 (t) | 41.40 (d) | 35.19 (d) | |
| 45.23 (t), | 40.40 (d), | 35.11 (d), | |
| 33.10 (d) | 32.81 (t) | 31.53 (t) | |
| 34.17 (d), | 32.29 (t), | 31.33 (t), | |
| 30.80 (t) | 28.60 (t), | 26.03 (d) | |
| 30.66 (t). | | 26.98 (d), | |
| 25.43 (t) | 18.93 (q) | 14.09 (q) | |
| 24.40 (t). | 20.57 (q), | 13.95 (q), | |
| 9.85 (q) | | | |
| 10.00 (q) | | | | the chart o which being shown in FIG. 5,

(10) $^1$H Nuclear Magnetic Resonance Spectrum: the chart of which being shown in FIG. 6,

(11) Thin Layer Chromatography:

| Stationary Phase | Developing Solvent | Rf Value |
|---|---|---|
| silica gel plate | ethyl acetate | 0.34 |

(12) Property of the Substance: neutral substance

(12) Property of the Substance
neutral substance

With regard to the FR-900525 substance, it is to be noted that in case of measurements of $^{13}$C and $^1$H nuclear magnetic resonance spectra, this substance showed pairs of the signals in various chemical shifts, however, in case of measurements of the thin layer chromatography and the high performance liquid chromatography, the FR-900525 substance showed a single spot in the thin layer chromatography and a single peak in the high performance liquid chromatography, respectively.

From the above physical and chemical properties and the success of the determination of the chemical structure of the FR-900506 substance, the FR-900525 substance could be determined to have the following chemical structure.

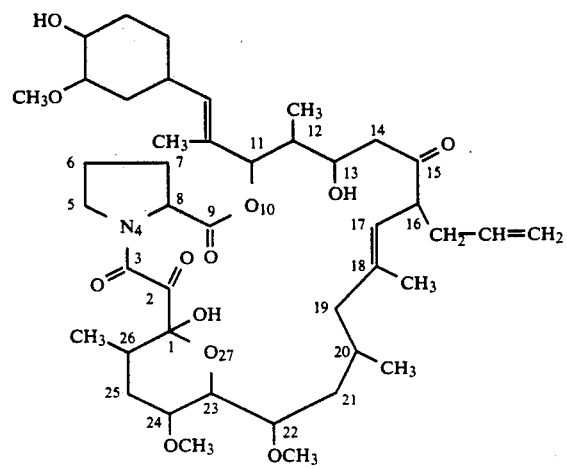

16-Allyl-1,13-dihydroxy-11-[2-(4-hydroxy-3-methoxycyclohexyl)-1-methylvinyl]-22,24-dimethoxy-12,18,20,26-tetramethyl-10,27-dioxa-4-azatricyclo-[21.3.1.04,8 heptacos-17-ene-2,3,9,15-tetraone

[B] The FR-900520 and FR-900523 substances of this invention can be produced by fermentation of FR-900520 and/or FR-900523 substance(s)-producing strain belonging to the genus Streptomyces such as *Streptomyces hygroscopicus* subsp yakushimaensis No. 7238 in a nutrient medium.

THE MICROORGANISM

The microorganism which can be used for the production of the FR-900520 and/or FR-900523 substances is FR-900520 and/or FR-900523 substance(s)-producing strain belonging to the genus Streptomyces, among which *Streptomyces hygroscopicus* subsp. yakushimaensis No. 7238 has been newly isolated from a soil sample collected at Yakushima, Kagoshima Prefecture, Japan.

A lyophilized sample of the newly isolated *Streptomyces hygroscopicus* subsp. yakushimaensis No. 7238 has been deposited with the Fermentation Research Institute, Agency of Industrial Science and Technology (No.1-3, Higashi 1-chome, Yatabemachi, Tsukuba-gun, Ibaraki Prefecture, Japan) under the number of FERM P-8043 (deposited date: Jan. 12, 1985), and then converted to Budapest Treaty route of the same depository on Oct. 19, 1985 under the new deposit number of FERM BP-928.

It is to be understood that the production of the novel FR-900520 and FR-900523 substances is not limited to the use of the particular organism described herein, which is given for the illustrative purpose only This invention also includes the use of any mutants which are capable of producing the FR-900520 and/or FR-900523 substance(s) including natural mutants as well as artificial mutants which can be produced from the described organism by conventional means such as irradiation of X-rays, ultra-violet radiation, treatment with N-methyl-N'-nitro-N-nitrosoguanidine, 2-aminopurine, and the like.

The *Streptomyces hygroscopicus* subsp. yakushimaensis No. 7238 has the following morpholdgical, cultural, biological and physiological characteristics.

[1]Morphological Characteristics:

The methods described by Shirling and Gottlieb (Shirling, E. B. and D. Gottlieb Methods for characterization of Streptomyces species. International Journal of Systematic Bacteriology, 16, 313-340, 1966) were employed principally for this taxonomic study.

Morphological observations were made with light and electron microscopes on cultures grown at 30° C. for 14 days on oatmeal agar, yeast-malt extract agar and inorganic salts-starch agar. The mature sporophores were moderately short and formed Retinaculiaperti and Spirales with about 20 spores in each chain. Hygroscopic spore mass were seen in the aerial mycelia on oatmeal agar and inorganic salts-starch agar Surface irregularities on spores were intermediate between very short, thick spines and warts.

[2] Cultural Characteristics:

Cultural characteristics were observed on ten kinds of media described by Shirling and Gottlieb as mentioned above, and by Waksman (Waksman, S. A.: The actinomycetes, vol. 2: Classification, identification and description of genera and species. The Williams and Wilkins Co., Baltimore, 1961).

The incubation was made at 30° C. for 14 days. The color names used in this study were based on Guide to Color Standard (manual published by Nippon Shikisai Kenkyusho, Tokyo). Colonies belonged to the gray color series when grown on oatmeal agar, yeast-malt extract agar and inorganic salts-starch agar. Soluble pigment was not produced in the examined media. The results are shown in Table 4.

TABLE 4

Cultural Characteristics of Strain No. 7238, *Streptomyces antimycoticus* IFO 12839 and *Streptomyces hygrosocopicus* subsp. *glebosus* IFO 13786

| Medium | | Cultural Characteristics | | |
|---|---|---|---|---|
| | | No. 7238 | IFO 12839 | IFO 13786 |
| Oatmeal Agar | G | Poor | Poor | Poor |
| | A | Grayish Yellow Brown | Grayish Yellow Brown | Grayish Yellow Brown |
| | R | Pale Yellow | Pale Yellow | Pale Yellow |
| | S | None | None | None |
| Yeast-Malt Extract Agar | G | Moderate | Abundant | Moderate |
| | A | Grayish White | Gray | Gray |
| | R | Pale Yellowish Brown | Pale Yellowish Brown | Dark Orange |
| | S | None | None | None |
| Inorganic Salts-Starch Agar | G | Moderate | Moderate | Moderate |
| | A | Gray to Black | Gray | Light Gray |
| | R | Pale Yellow Orange | Yellowish Gray | Pale Yellow Orange |
| | S | None | None | None |
| Glucose-Asparagine Agar | G | Moderate | Moderate | Moderate |
| | A | Grayish White | Gray | White |
| | R | Pale Yellow Orange | Pale Yellow Orange | Pale Yellow Orange |
| | S | None | None | None |
| Glycerin-Asparagine Agar | G | Moderate | Moderate | Moderate |
| | A | White | Gray | Light Gray |
| | R | Yellowish Gray | Yellowish Gray | Grayish Yellow Brown |
| | S | None | None | None |
| Czapek Agar | G | Moderate | Moderate | Moderate |
| | A | Grayish White | Grayish White | White |
| | R | Pale Yellowish Brown | Pale Yellowish Brown | Pale Yellowish Brown |
| | S | None | None | None |
| Nutrient Agar | G | Moderate | Moderate | Moderate |
| | A | Grayish White | Grayish White | None |
| | R | Pale Yellow | Pale Yellow | Pale Yellow |
| | S | None | None | None |
| Potato-Dextrose Agar | G | Moderate | Moderate | Moderate |
| | A | White, Poor | Pale Reddish Brown | Pale Pink to White |
| | R | Pale Yellow Orange | Pale Yellow Orange | Pale Yellowish Brown |
| | S | None | None | None |
| Tyrosin Agar | G | Moderate | Moderate | Moderate |
| | A | White | Grayish White | Gray to Black |
| | R | Pale Yellowish Brown | Brown | Pale Yellowish Brown |
| | S | None | Brown | None |
| Peptone-Yeast Extract-Iron Agar | G | Moderate | Moderate | Moderate |
| | A | None | Grayish White | None |
| | R | Pale Yellow | Pale Yellow | Colorless |
| | S | None | None | None |

Abbreviation:
G = Growth,
A = Aerial Mass Color,
R = Reverse Side Color,
S = Soluble Pigment, The cell wall analysis was performed by the methods of Becker et al. (Becker, B., M. P. Lechevalier, R. E. Gordon and H. A. Lechevalier: Rapid differentiation between Nocardia and Streptomyces by paper chromatography of whole cell hydrolysates: Appl Microbiol., 12, 421-423, 1964) and Yamaguchi (Yamaguchi, T.: Comparison of the cell wall composition of morphologically distinct actinomycetes: J. Bacteriol., 89, 444-453, 1965). Analysis of whole cell hydrolysates of the strain No 7238 showed the presence of LL-diaminopimelic acid Accordingly, the cell wall of this strain is believed to be of type I.

[3] Biological and Physiological Properties:

Physiological properties of the strain No. 7238 were determined according to the methods described by Shirling and Gottlieb as mentioned above The results are shown in Table 5. Temperature range and optimum temperature for growth were determined on yeast-malt extract agar using a temperature gradient incubator (made by Toyo Kagaku Sangyo Co., Ltd.). Temperature range for growth was from 18° to 36° C. with optimum temperature at 28° C. Starch hydrolysis and gelatin liquefaction were positive No melanoid pigment was produced.

TABLE 5

Physiological Properties of Strain No. 7238, *Streptomyces antimycoticus* IFO 12839 and *Streptomyces hygroscopicus* subsp. *glebosus* IFO 13786

| Physiological properties | No. 7238 | IFO 12839 | IFO 13786 |
|---|---|---|---|
| Temperature Range for Growth | 19° C.–36° C. | 18° C.–38° C. | 16° C.–35° C. |
| Optimum Temperature | 28° C. | 28° C. | 27° C. |
| Nitrate Reduction | Negative | Negative | Negative |
| Starch Hydrolysis | Postive | Postive | Positive |
| Milk Coagulation | Negative | Negative | Negative |
| Milk Peptonization | Negative | Negative | Positive |
| Melanin Production | Negative | Negative | Negative |
| Gelatin Liquefaction | Positive | Postive | Positive |
| $H_2S$ Production | Negative | Negative | Negative |
| Urease Activity | Negative | Negative | Negative |
| NaCl Tolerance (%) | 7%<, <10% | 7%<, <10% | 5%<, <% |

Utilization of carbon sources was examined according to the methods of Pridham and Gottlieb (Pridham, T. G. and D. Gottlieb: The utilization of carbon compounds by some Actinomycetales as an aid for species determination: J. Bacteriol., 56, 107–114, 1948). The growth was observed after 14 days incubation at 30° C.

Summarized carbon sources utilization of this strain is shown in Table 6. D-Glucose, sucrose, lactose, maltose, D-trehalose, inositol, inulin and salicin could be utilized by the strain No. 7238.

TABLE 6

Carbon Sources Utilization of Strain No. 7238, *Streptomyces antimycoticus* IFO 12839 and *Streptomyces hygroscopicus* subsp. *glebosus* IFO 13786

| Carbon Sources | No. 7238 | IFO 12839 | IFO 13786 |
|---|---|---|---|
| D-Glucose | + | + | + |
| Sucrose | + | + | + |
| Glycerin | − | + | + |
| D-Xylose | − | ± | + |
| D-Fructose | − | + | + |
| Lactose | + | + | − |
| Maltose | + | − | + |
| Rhamnose | − | + | − |
| Raffinose | − | + | + |
| D-Galactose | − | + | + |
| L-Arabinose | − | ± | ± |
| D-Mannose | − | + | + |
| D-Trehalose | + | ± | + |
| Inositol | + | + | + |
| D-Mannitol | − | + | + |
| Inulin | + | + | − |
| Cellulose | ± | − | − |
| Salicin | + | + | − |
| Chitin | ± | − | − |
| Sodium Citrate | − | − | ± |
| Sodium Succinate | − | + | + |
| Sodium Acetate | − | − | − |

Symbols:
+: utilization
±: doubtful utilization
−: no utilization

Microscopic studies and cell wall composition analysis of the strain No. 7238 indicate that this strain belongs to the genus Streptomyces Waksman and Henrici 1943.

Accordingly, a comparison of this strain was made with various Streptomyces species in the light of the published descriptions [International Journal of Systematic Bacteriology, 18, 69 to 189, 279 to 392 (1968) and 19, 391 to 512 (1969), and Bergy's Manual of Determinative Bacteriology 8th Edition (1974)].

As a result of the comparison, the strain No. 7238 is considered to resemble *Streptomyces antimycoticus* Waksman 1957 and *Streptomyces hygroscopicus* subsp. glebosus Ohmori, et. al. 1962. Therefore, the cultural characteristics of the strain No. 7238 were further compared with the corresponding *Streptomyces antimycoticus* IFO 12839 and *Streptomyces hygroscopicus* subsp. glebosus IFO 13786 as shown in the above Tables 4, 5 and 6. From further comparison, the strain No. 7238 could be differentiated from *Streptomyces antimycoticus* IFO 12839 and *Streptomyces hygroscopicus* subsp. glebosus IFO 13786 in the following points.

(i) Difference from *Streptomyces antimycoticus* IFO 12839

Cultural characteristics of the strain No. 7238 are different from the *Streptomyces antimycoticus* IFO 12839 on yeast-malt extract agar, glucose-asparagine agar, glycerinasparagine agar, potato-dextrose agar and tyrosine agar.

In carbon sources utilization, the strain No 7238 can utilize maltose, but the *Streptomyces antimycoticus* IFO 12839 can not utilize it. And, the strain No. 7238 can not utilize glycerin, D-fructose, rhamnose, raffinose, D-galactose, D-mannose, mannitol and sodium succinate, but the *Streptomyces antimycoticus* IFO 12839 can utilize them.

(ii) Difference from *Streptomyces hygroscopicus* subsp. glebosus IFO 13786

Cultural characteristics of the strain No. 7238 are different from the *Streptomyces hygroscopicus* subsp. glebosus IFO 13786 on yeast-malt extract agar, potato-dextrose agar and tyrosine agar.

Milk peptonization of the strain No. 7238 is negative, but that of the *Streptomyces hygroscopicus* subsp. glebosus IFO 13786 is positive The strain No. 7238 can grow in the presence of 7% NaCl, but the *Streptomyces hygroscopicus* subsp. glebosus IFO 13786 can not grow under the same condition.

In carbon sources utilization, the strain No. 7238 can utilize lactose, inulin and salicin, but the *Streptomyces hygroscopicus* subsp. glebosus IFO 13786 can nbt utilize them. And, the strain No. 7238 can not utilize glycerin, D-xylose, D-fructose, raffinose, D-galactose, D-mannose, mannitol and sodium succinate, but the *Streptomyces hygroscopicus* subsp. glebosus IFO 13786 can utilize them.

However, the strain No. 7238 forms hygroscopic spore mass in the aerial mycelia on oatmeal agar and inorganic salts-starch agar, and further morphological and cultural characteristics of the strain No. 7238 are similar to the *Streptomyces hygroscopicus* subsp. glebosus IFO 13786. Tnerefore, the strain No. 7238 is considered to belong to *Streptomyces hygroscopicus*, but the strain No. 7238 is different from the *Streptomyces hygroscopicus* subsp. glebosus IFO 13786, though this known strain is the most similar to the strain No. 7238 in *Streptomyces hygroscopicus* subspecies. From the above facts, the strain No. 7238 is considered to be a new subspecies of *Streptomyces hygroscopicus* and has been designated as

*Streptomyces hygroscopicus* subsp yakushimaensis subsp. nov., referring to the soil collected at Yakushima, from which the organism was isolated.

PRODUCTION OF FR-900520 and FR-900523 SUBSTANCES

The novel FR-900520 and/or FR-900523 substance(s) can be produced by culturing FR-900520 and/or FR-900523 substance(s)-producing strain belonging to the genus Streptomyces (e.g. *Streptomyces hygroscopicus* subsp. yakushimaensis No. 7238, FERM BP-928) in a nurrient medium.

In general, the FR-900520 and/or FR-900523 substance(s) can be produced by culturing the FR-900520 and/or FR-900523 substance(s)-producing strain in an aqueous nutrient medium containing sources of assimilable carbon and nitrogen, preferably under aerobic conditions (e.g. shaking culture, submerged culture, etc.).

The preferred sources of carbon in the nutrient medium are carbohydrates such as glucose, sucrose, lactose, glycerin, starch, dextrin, and the like. Other sources which may be included are maltose, D-trehalose, inositol, inulin, salicin, and the like.

The preferred sources of nitrogen are yeast extract, peptone, gluten meal, cottonseed meal, soybean meal, corn steep liquor, dried yeast, wheat germ, feather meal, peanut powder etc., as well as inorganic and organic nitrogen compounds such as ammonium salts (e.g. ammonium nitrate, ammonium sulfate, ammonium phosphate, etc.), urea, amino acid, and the like.

The carbon and nitrogen sources, though advantageously employed in combination, need not be used in their pure form, because less pure materials which contain traces of growth factors and considerable quantities of mineral nutrients, are also suitable for use When desired, there may be added to the medium mineral salts such as sodium or calcium carbonate, sodium or potassium phosphate, sodium or potassium chloride, sodium or potassium iodide, magnesium salts, copper salts, cobalt salt and the like. If necessary, especially when the culture medium foams seriously, a defoaming agent, such as liquid paraffin, fatty oil, plant oil, mineral oil or silicone may be added.

As the conditions for the production of the FR-900520 and FR-900523 substances in massive amounts, submerged aerobic cultural conditions are preferred therefor For the production in small amounts, a shaking or surface culture in a flask or bottle is employed Furthermore, when the growth is carried out in large tanks, it is preferable to use the vegetative form of the organism for inoculation in the production tanks in order to avoid growth lag in the process of production of the FR-900520 and FR-900523 substances. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of the FR-900520 and FR-900523 substances.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 50 hours to 150 hours, which may be varied according to fermentation conditions and scales.

Thus produced FR-900520 and/or FR-900523 substance(s) can be recovered from the culture medium by conventional means which are commonly used for the recovery of other known biologically active substances. The FR-900520 and FR-900523 substances produced are mainly found in the cultured mycelium, and accordingly the FR-900520 and FR-900523 substances can be isolated and purified from the mycelium, which are obtained by filtering or centrifuging the cultured broth, by a conventional method such as concentration under reduced pressure, lyophilization, extraction with a conventional solvent, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, re-crystallization, and the like.

Particularly, the FR-900520 substance and the FR-900523 substance can be separated by dissolving the materials containing both products produced by fermentation in an appropriate solvent such as ethyl acetate, n-hexane, and the like, and then by subjecting said solution to chromatography, for example, on silica gel in a column with an appropriate organic solvent such as ethyl acetate and n-hexane, or a mixture thereof And each of the FR-900520 substance and the FR-90523 substance thus separated can be further purified by a conventional method, for example, recrystallization, re-chromatography, high performance liquid chromatorgraphy, and the like.

PHYSICAL AND CHEMICAL PROPERTIES OF FR-900520 and FR-900523 SUBSTANCES

RF-900520 Sbustance (1) Form and Color:
colorless plates
(2) Elemental Analysis:
C: 64.81%, H: 8.82%, N: 1.55%
(3) Color Reaction:
Positive: cerium sulfate reaction, sulfuric acid reaction, Ehrlich reaction, Dragendorff reaction and iodine vapor reaction
Negative: ferric chloride reaction, ninhydrin reaction and Molish reaction
(4) Solubility:
Soluble: methanol, ethanol, acetone, ethyl acetate, chloroform, diethyl ether and benzene
Sparingly Soluble: n-hexane, petroleum ether
Insoluble: water
(5) Melting Point:
163°–165° C.
(6) Specific Rotation:
$[\alpha]_D^{23}$: −84.1° (c=1.0, $CHCl_3$)
(7) Ultraviolet Absorption Spectrum:
end absorption
(8) Infrared Absorption Spectrum:
$CHCL_3 \gamma$max: 3680, 3575, 3520, 2940, 2875, 2825, 1745, 1725, 1700, 1647, 1610(sh), 1452, 1380, 1350, 1330, 1285, 1170, 1135, 1090, 1030, 1005, 990, 980(sh), 960(sh), 913, 908(sh) $cm^{-1}$ (9) ¹³C Nuclear Magnetic Resonance Spectrum:

| δ (ppm, CDCl₃): | 213.04 (s), | 196.21 (s) 193.23 (s), | 169.07 (s) 168.85 (s), |
|---|---|---|---|
| | 164.92 (s) 165.97 (s), | 138.67 (s) 139.53 (s), | 132.46 (s) 131.98 (s), |
| | 130.20 (d) 130.08 (d), | 123.42 (d) 123.59 (d), | 97.28 (s) 98.75 (s), |
| | 84.37 (d), | 77.80 (d) 78.24 (d), | 75.53 (d) 76.98 (d), |
| | 73.92 (d), | 73.69 (d), | 73.11 (d) 72.72 (d), |
| | 70.11 (d) 69.21 (d), | 57.02 (q), | 56.60 (q) 57.43 (q), |
| | 56.23 (q) 55.98 (q), | 56.72 (d) 52.91 (d), | 55.10 (d) 54.90 (d), |
| | 48.90 (t) 48.57 (t), | 40.19 (d) 40.63 (d), | 27.67 (t) 26.32 (t), |
| | 26.51 (d) 26.44 (d), | 24.60 (t), | 21.19 (t) 20.86 (t), |
| | 20.47 (q) 19.75 (q), | 16.21 (q) 15.97 (q), | 15.83 (q) 15.94 (q), |
| | 14.04 (q) 14.16 (q), | 11.68 (q), | 9.64 (q) 9.93 (q), | the chart of which being shown in FIG. 7,

(10) ¹H Nuclear Magnetic Resonance Spectrum:
the chart of which being shown in FIG. 8,

(11) Thin Layer Chromatorgraphy:

| Stationary Phase | Developing Solvent | Rf Values |
|---|---|---|
| silica gel plate | chloroform :methanol (20:1, v/v) | 0.38 |
| | ethyl acetate | 0.51 |

(12) Property of the Substance: neutral substance

(12) Property of the Substance:
neutral substance

With regard to the FR-900520 substance, it is to be noted that in case of measurements of ¹³C and ¹H nuclear magnetic resonance spectra, this substance shows pairs of the signals in various chemical shifts, however, in case of measurements of the thin layer chromatography and the high performance liquid chromatography, the FR-900520 substance showed a single spot in the thin layer chromatography and a single peak in the high performance liquid chromatography, respectively.

From the above physical and chemical properties and the success of the determination of the chemical structure of the FR-900506 substance, the FR-900520 substance could be determined to have the following chemical structure.

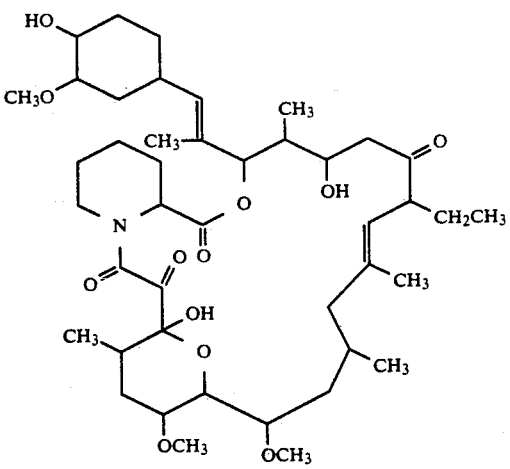

17Ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18ene-2,3,10,16-tetraone FR-900523 Substance (1) Form and Color:
colorless needles
(2) Elemental Analysis:
C: 64.57%, H: 8.84%, N: 1.81%
(3) Color Reaction:
Positive: cerium sulfate reaction, sulfuric acid reaction, Ehrlich reaction, Dragendorff reaction and iodine vapor reaction
Negative: ferric chloride reaction and ninhydrin reaction
(4) Solubility:
Soluble : methanol, ethanol, acetone, ethyl acetate, chloroform, diethyl ether and benzene
Sparingly Soluble: n-hexane and petroleum ether
Insoluble : water
(5) Melting Point
152°–154 ° C.
(6) Specific Rotation
$[\alpha]_D^{23}$: −73.0° (C=0.65, CHCl₃)
(7) ULtraviolet Absorption Spectrum:
end absorption
(8) Infrared Absorption Spectrum:
CHCl₃γmax: 3670, 3580, 3510, 2930, 2875, 2825, 1745, 1722, 1700, 1647, 1450, 1830, 1350, 1330, 1307, 1285, 1170, 1135, 1090, 1050, 1030, 1000, 990, 978, 960, 930, 915, 888, 870, 850 cm$^{-1}$
(9) ¹³C Nuclear Magnetic Resonance Spectrum

| δ (ppm, CDCl₃): | 213.82 (s) 213.32 (s), | 196.31 (s) 193.34 (s), | 168.96 (s) 168.85 (s), |
|---|---|---|---|
| | 164.84 (s) 165.98 (s), | 137.80 (s) 138.41 s), | 132.89 (s) 131.96 (s), |
| | 129.62 (d) 130.03 (d), | 124.51 (d) 124.84 (d), | 97.13 (s) 98.67 (s), |
| | 84.38 (d), | 76.69 (d) 78.06 (d), | 75.45 (d) 76.91 (d), |
| | 73.89 (d) 73.70 (d), | 73.70 (d), | 73.09 (d) 72.84 (d), |
| | 70.40 (d) | 56.75 (d) | 56.93 (q) |

| | | |
|---|---|---|
| 69.24 (d), | 52.89 (d), | 57.43 (q), |
| 56.61 (q) <br> 56.56 (q), | 56.24 (q) <br> 55.94 (q), | 48.58 (t) <br> 48.32 (t), |
| 47.14 (d) <br> 47.38 (d), | 40.23 (d) <br> 40.65 (d), | 27.85 (t) <br> 26.32 (t), |
| 26.48 (d) <br> 26.64 (d), | 24.68 (t), | 21.33 (t) <br> 20.83 (t), |
| 20.63 (q) <br> 19.77 (q), | 16.24 (q) <br> 16.34 (q), | 15.70 (q) <br> 15.96 (q), |
| 15.51 (q) <br> 15.96 (q), | 14.31 (q) <br> 14.18 (q), | 9.64 (q) <br> 10.04 (q), | the chart of which being shown in FIG. 9,
(10) ¹H Nuclear Magnetic Resonance Spectrum: the chart of which being shown in FIG. 10,
(11) Thin Layer Chromatography:

| Stationary Phase | Developing Solvent | Rf Values |
|---|---|---|
| silica gel plate | chloroform :methanol (20:1, v/v) | 0.38 |
| | ethyl acetate | 0.51 |

(12) Property of the Substance: neutral substance

With regard to the FR-900523 substance, it is to be noted that in case of measurements of ¹³C and ¹H nuclear magnetic resonance spectra, this substance shows pairs of the signals in various chemical shifts, however, in case of measurements of the thin layer chromatography and the high performance liquid chromatography, the FR-900523 substance showed a single spot in the thin layer chromatography and a single peak in the high performance liquid chromatography, respectively.

From the above physical and chemical properties and the success of the determination of the chemical structure of the FR-900506 substance, the FR-900523 substance could be determined to have the following chemical structure.

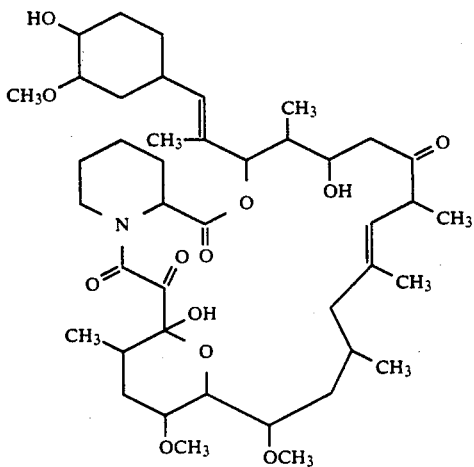

1,14-Dihydroxy-12-[2-(4-hydroxy-3-methoxycyclohexyl)-1-methylvinyl]-23,25-dimethoxy-13,19,17,21,27-pentamethyl-11,28-dioxa-4-axatricyclo[22.3.1.0$^{4,9}$]-octacos-18-ene-2,3,10,16-tetraone

[II] Synthetic Processes (1) Process 1: (Introduction of Hydroxy-Protective Group)

The compound (Ib) or a salt thereof can be prepared by introducing a hydroxy-protective group into the compound (Ia) or a salt thereof.

Suitable introducing agent of the hydroxy-protective group used in this reaction may be a conventional one such as di(lower)alkyl sulfoxide, for example, lower alkyl methyl sulfoxide (e.g. dimethyl sulfoxide, ethyl methyl sulfoxide, propyl methyl sulfoxide, isopropyl methyl sulfoxide, butyl methyl sulfoxide, isobutyl methyl sulfoxide, hexyl methyl sulfoxide, etc.), trisubstituted silyl compound such as tri(lower)alkylsilyl halide (e.g. trimethylsilyl chloride, triethylsilyl bromide, tributylsilyl chloride, tert-butyl-dimethylsilyl chloride, etc.), lower alkyl-diarylsilyl halide (e.g. methyl-diphenylsilyl chloride, ethyl-diphenylsilyl bromide, propyl-ditolylsilyl chloride, tert-butyl-diphenylsilyl chloride, etc ), and acylating agent which is capable of introducing the acyl group as mentioned before such as carboxylic acid, sulfonic acid, carbamic acid and their reactive derivative, for example, an acid halide, an acid anhydride, an activated amide, an activated ester, isocyanate, and the like Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic trifluoroacetic acid, etc.), aromatic carboxylic acid (e.g benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), isocyanate, and the like.

In this reaction, in case that the di(lower)alkyl sulfoxide is used as an introducing agent of the hydroxy-protective group, the reaction is usually conducted in the presence of lower alkanoic anhydride such as acetic anhydride.

Further, in case that the trisubstituted silyl compound is used as an introducing agent of the hydroxy-protective group, the reaction is preferable conducted in the presence of a conventional condensing agent such as imidazole, and the like.

Still further, in case that the acylating agent is used as an introducing agent of the hydroxy-protective group, the reaction is preferably conducted in the presence of an organic or inorganic base such as alkali metal (e.g.

lithium, sodium, potassium, etc ), alkaline earth metal (e.g. calcium, etc.), alkali metal hydride (e.g sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc ), trialkylamine (e.g. triethylamine, etc.), pyridine compound (e.g. pyridine, lutidine, picoline, 4-N,N-dimethylaminopyridine, etc.), quinoline, and the like.

In case that the acylating agent is used in a free form or its salt in this reaction, the reaction is preferably conducted in the presence of a conventional condensing agent such as a carbodiimide compound [e.g. N,N'-dicyclohexylcarbodiimide, N-cyclohexyl-N'-(4-diethylaminocyclohexyl)-carbodiimide, N,N'-diethylcarbodiimide, N,N'-diisopropylcarbodiimide, N-ethyl-N'-(3-dimethylaminopropyl)-carbodiimide, etc.], a ketenimine compound (e.g N,N'-carbonylbis(2-methylimidazole), pentamethyleneketene-N-cyclohexylimine, diphenylketene-N-cyclohexylimine, etc ); an olefinic or acetylenic ether compounds (e.g. ethoxyacetylene, β-cyclovinylethyl ether), a sulfonic acid ester of N-hydroxybenzotriazole derivative [e.g. 1-(4-chlorobenzenesulfonyloxy)6-chloro-1H-benzotriazole, etc.], and the like.

The reaction is usually conducted in a conventional solvent which does not adversely influence the reaction such as water, acetone, dichloromethane, alcohol (e.g. methanol, ethanol, etc ), tetrahydrofuran, pyridine, benzene, N,N-dimethylformamide, etc., or a mixture thereof, and further in case that the base or the introducing agent of the hydroxy-protective group is in liquid, it can also be used as a solvent The reaction temperature is not critical and the reaction is usually conducted under from cooling to heating This process includes, within a scope thereof, a case that during the reaction, the hydroxy group for $R^2$ of the compound (Ia) may occasionally be transformed into the corresponding protected hydroxy group in the object compound (Ib).

Further, this process also includes, within a scope thereof, a case that when the di(lower)alkyl sulfoxide is used as an introducing agent of the hydroxy-protective group in the presence of lower alkanoic anhydride, the compound (Ia) having a partial structure of the formula:

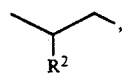

wherein $R^2$ is hydroxy, may occasionally be oxidized during the reaction to give the compound (Ib) having a partial structure of the formula

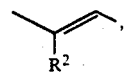

wherein $R^2$ is hydroxy.

(2) Process 2: (Introduction of Hydroxy-Protective Group)

The compound (Id) or a salt thereof can be prepared by introducing a hydroxy-protective group into the compound (Ic) or a salt thereof The reaction can be conducted by substantially the same method as that of Process 1, and therefore the reaction conditions (e.g. base, condensing agent, solvent, reaction temperature, etc.) are referred to those of Process 1.

This process includes, within a scope thereof, a case that during the reaction, the hydroxy group for $R^1$ of the compound (Ic) may frequently be transformed into the corresponding protected hydroxy group in the object compound (Id).

(3) Process 3: (Formation of Double Bond)

The compound (If) or a salt thereof can be prepared by reacting the compound (Ie) or a salt thereof with a base.

Suitable base to be used in this reaction may include one as exemplified in Process 1.

This reaction can also be conducted by reacting the compound (Ie), where $R^2$ is hydroxy, with an acylating agent in the presence of a base.

The reaction is usually conducted in a conventional solvent which does not adversely influence the reaction such as water, acetone, dichloromethane, alcohol (e.g. methanol, ethanol, propanol, etc ), tetrahydrofuran, pyridine, N,N-dimethylformamide, etc , or a mixture thereof, and further in case that the base is in liquid, it can also be used as a solvent.

The reaction temperature is not critical and the reaction is usually conducted under from cooling to heating.

(4) Process 4: (Oxidation of Hydroxyethylene Group)

The compound (Ih) or a salt thereof can be prepared by oxidizing the compound (Ig) or a salt thereof.

The oxidizing agent to be used in this reaction may include di(lower)alkyl sulfoxide such as those given in Process 1.

This reaction is usually conducted in the presence of lower alkanoic anhydride such as acetic anhydride in a conventional solvent which does not adversely influence the reaction such as acetone, dichloromethane, ethyl acetate, tetrahydrofuran, pyridine, N,N-dimethylformamide, etc., or a mixture thereof, and further in case that the lower alkanoic anhydride is in liquid, it can also be used as a solvent.

The reaction temperature is not critical and the reaction is usually conducted under from cooling to heating.

This process includes, within a scope thereof, a case that during the reaction the hydroxy group for $R^1$ of the starting compound (Ig) may occasionally be transformed into 1-(lower alkylthio)(lower)alkyloxy group in the object compound (Ih).

(5) Process 5: (Reduction of Allyl Group)

The compound (Ij) or a salt thereof can be obtained by reducing the compound (Ii) or a salt thereof.

Reduction in this process can be conducted by a conventional method which is capable of reducing an allyl group to a propyl group, such as catalytic reduction, or the like.

Suitable catalysts used in catalytic reduction are conventional ones such as platinum catalysts (e g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc ), and the like.

The reduction is usually conducted in a conventional solvent which does not adversely influence the reaction such as water, methanol, ethanol, propanol, pyridine, ethyl acetate, N,N-dimethylformamide, dichloromethane, or a mixture thereof.

The reaction temperature of this reduction is not critical and the reaction is usually conducted under from cooling to warming.

(6) Process 6: (Removal of the carboxy-protective group)

The compound (I±) or a salt thereof can be prepared by removing the carboxy-protective group from the compound (Ik) or a salt thereof.

The removal reaction in this process can be conducted in a conventional manner which is capable of transforming a tri(lower)alkylsilyl(lower)alkoxycarbonyl group to a carboxy group, that is, in the presence of tetra(lower)alkylammonium fluoride (e.g. tetrabutylammonium fluoride, etc.), potassium fluoride, hydrogen fluoride, and the like.

This reaction is usually conducted in a conventional solvent which does not adversely influence the reaction such as tetrahydrofuran, and the like.

The reaction temperature is not critical and the reaction is usually conducted under from cooling to warming.

The object tricyclo compounds (I) obtained according to the synthetic processes 1 to 6 as explained above can be isolated and purified in a conventional manner, for example, extraction, precipitation, fractional crystallization, recrystallization, chromatography, and the like.

Suitable salts of the compounds (I) and (Ia) to (I±) may include pharamaceutically acceptable salts such as basic salts, for example, alkali metal salt (e.g. sodium salt, potassium salt, etc.), alkaline earth metal salt (e.g. calcium salt, magnesium salt, etc.), ammonium salt, amine salt (e.g. triethylamine salt, N-benzyl-N-methylamine salt, etc.) and other conventional organic salts.

It is to be noted that in the aforementioned reactions in the synthetic processes 1 to 6 or the post-treatment of the reaction mixture therein, the conformer and/or stereo isomer(s) due to asymmetric carbon atom(s) or double bond(s) of the starting and object compounds may occasionally be transformed into the other conformer and/or stereoisomer(s), and such cases are also included within the scope of the present invention.

The tricyclo compounds (I) of the present invention possess pharmacological activities such as immunosuppressive activity, antimicrobial activity, and the like, and therefore are useful for the treatment and prevention of the resistance by transplantation of organs or tissues such as heart, kidney, liver, medulla ossium, skin, etc., graft-versus-host diseases by medulla ossium transplantation, autoimmune diseases such as rheumatoid arthritis, systemic lupus erythematosus, Hashimoto's thyroiditis, multiple sclerosis, myasthenia gravis, type I diabetes, uveitis, etc., infectious diseases caused by pathogenic microorganisms, and the like.

As examples for showing such pharmacological activities, some pharmacological test data of the tricyclo compounds are illustrated in the following.

Test 1

Suppression of Tricyclo Compounds (I) in in vitro Mixed Lymphocyte Reaction (MLR)

The MLR test was performed in microtiter plates, with each well containing $5 \times 10^5$ C57BL/6 responder cells (H-$2^b$), $5 \times 10^5$ mitomycin C treated (25μg/ml mitomycin C at 37° C. for 30 minutes and washed three times with RPMI 1640 medium) BALB/C stimulator cells (H-$2^d$) in 0.2 ml RPMI 1640 medium supplemented with 10% fetal calf serum, 2 mM sodium hydrogen carbonate, penicillin (50 unit/ml) and streptomycin (50 μg/ml). The cells were incubated at 37° C. in humidified atmosphere of 5% carbon dioxide and 95% of air for 68 hours and pulsed with 3H-thymidine (0.5 μCi) 4 hours before the cells were collected. The object compound of this invention was dissolved in ethanol and further diluted in RPMI 1640 medium and added to the cultures to give final concentrations of 0.1 μg/ml or less.

The results are shown in Tables 7 to 10. The tricyclo compounds of the present invention suppressed mouse MLR.

TABLE 7

Effect of the FR-900506 Substance on MLR

| FR-900506 concentration (ng/ml) | Radioactivities (mean C.P.M. ± S.E.) | Suppression (%) | IC$_{50}$ (ng/ml) |
|---|---|---|---|
| 2.5 | 54 ± 4 | 99.5 | |
| 1.25 | 168 ± 23 | 98.3 | |
| 0.625 | 614 ± 57 | 93.8 | |
| 0.313 | 3880 ± 222 | 60.9 | 0.26 |
| 0.156 | 5490 ± 431 | 44.7 | |
| 0.078 | 7189 ± 365 | 27.6 | |
| 0 | 9935 ± 428 | 0 | |

TABLE 8

Effect of FR-900520 Substance on MLR

| FR-900520 concentration (ng/ml) | Radioactivities (mean C.P.M. ± S.E.) | Suppression (%) | IC$_{50}$ (ng/ml) |
|---|---|---|---|
| 100 | 175 ± 16 | 99.2 | |
| 10 | 515 ± 55 | 97.8 | |
| 1 | 2744 ± 527 | 88.1 | 0.38 |
| 0.500 | 9434 ± 1546 | 59.2 | |
| 0.25 | 14987 ± 1786 | 35.1 | |
| 0 | 23106 ± 1652 | 0 | |

TABLE 9

Effect of FR-900523 Substance on MLR

| FR-900523 concentration (ng/ml) | Radioactivities (mean C.P.M. ± S.E.) | Suppression (%) | IC$_{50}$ (ng/ml) |
|---|---|---|---|
| 100 | 25 ± 12 | 99.9 | |
| 10 | 156 ± 37 | 99.3 | |
| 1 | 5600 ± 399 | 75.8 | 0.5 |
| 0.500 | 11624 ± 395 | 49.7 | |
| 0.250 | 17721 ± 1083 | 23.3 | |
| 0 | 23106 ± 1052 | 0 | |

TABLE 10

Effect of the FR-900525 Substance on MLR

| FR-900525 concentration (ng/ml) | Radioactivities (mean C.P.M. ± S.E.) | Suppression (%) | IC$_{50}$ (ng/ml) |
| --- | --- | --- | --- |
| 100 | 469 ± 56 | 97.0 | |
| 10 | 372 ± 32 | 97.6 | |
| 5 | 828 ± 369 | 94.7 | 1.55 |
| 2.5 | 3564 ± 512 | 77.4 | |
| 1.2 | 10103 ± 421 | 35.8 | |
| 0 | 15741 ± 411 | 0 | |

Test 2

Antimicrobial activities of Tricyclo Compounds (I)

Antimicrobial activities of the tricyclo compunds (I) against various fungi were determined by a serial agar dilution method in a Sabouraud agar. Minimum inhibitory concentration (MIC) were expressed in terms of μg/ml after incubation at 30° C. for 24 hours.

Tricyclo compounds of the present invention showed antimicrobial activities against fungi, for example, *Aspergillus fumigatus* IFO 5840 and *Fusarium oxysporum* IFO 5942 as described in the following Tables 11 and 12.

TABLE 11

**MIC values (μg/ml) of Tricyclo Compounds (I) against *Aspergillus fumigatus* IFO 5840**

| Substances | MIC (μg/ml) |
| --- | --- |
| FR-900506 | 0.025 |
| FR-900520 | 0.1 |
| FR-900523 | 0.3 |
| FR-900525 | 0.5 |

TABLE 12

**MIC values (μg/ml) of Tricyclo Compounds (I) of against *Fusarium oxysporum***

| Substances | MIC (μg/ml) |
| --- | --- |
| FR-900506 | 0.05 |
| FR-900525 | 1 |

Test 3

Effect of Tricyclo Compounds (I) on Skin Allograft Survival in Rats

Vental allografts from donor (Fischer) rats were grafted onto the lateral thoracic area of recipient (WKA) rats. The dressings were removed on day 5. The grafts were inspected daily until rejection which ws defined as more than 90% necrosis of the graft epitherium.

The FR-900506 substance was dissolved in olive oil and administered intramuscularly for 14 consecutive days, beginning at the day of transplantation.

As shown in Table 13, all skin allografts were rejected within 8 days in rats treated with olive oil intramuscularly for 14 consecutive days, but daily treatment with the FR-900506 substance learly prolonged skin allograft survival.

TABLE 13

Effect of FR-900506 Substance on Skin Allograft Survival

| | Dose (mg/kg) | Number of Animals | Skin Allograft Survival Day |
| --- | --- | --- | --- |
| Control | — | 11 | 7,7,7,7,7,7,8,8,8,8,8 |
| (olive oil) FR-900506 Substance | 1 | 8 | 19,19,19,20,21,21,22,22 |
| | 3.2 | 6 | 22,23,23,26,27,35 |
| | 10 | 5 | 56,61,82,85,89 |

Test 4

Effect of Tricylo Compounds (I) on Type II Collagen-Induced-Arthritis in Rats

Collagen was dissolved in cold 0.01M acetic acid at a concentration of 2 mg/ml. The solution was emulsified in an equal volume of incomplete Freund's adjuvant. A total volume of 0.5 ml of the cold emulsion was injected intradermally at several sites on the back and one or two sites in to the tail of female Lewis rats. The FR-900506 substance was dissolved in olive oil and administered orally. Control rats immunized with same amount of type II collagen received oral adminstrations of olive oil alone. Incidences of the arthritis were observed.

The test results are shown in Table 14. The inflamatory polyarthritis was induced in all rats treated with olive oil for 14 days starting on the same day as the type II collagen immunization.

Daily treatment with the FR-900506 substance for 14 days gave complete suppression of arthritis induction during an observation period of 3 weeks.

TABLE 14

Effect of FR-900506 Substance on Type II Collagen-induced-Arthritis in Rats

| | Dose (mg/kg per day) | Incidence of Arthritis |
| --- | --- | --- |
| Control (olive oil) | — | 5/5 |
| FR-900506 Substance | 3.2 | 0/5 |

Test 5

Effect of Tricylo Compounds (I) on Experimental Allergic Encephalomyelytis (EAE) in SJL/J Mice Spinal cord homogenate was prepared from SJL/J mice. The spinal cords were removed by insufflation, mixed with an approximately equal volume of water and homogenized at 4° C. An equal volume of this cold homogenate (10 mg/ml) was emulsified with complete Freund's adjuvant (CFA) containing 0.6 mg/ml of *Mycobacterium tuberculosis* H37RA.

EAE was induced by two injections of 0.2 ml of spinal cord-CFA emulsion into SJL/J mice on day 0 and day 13. All mice used in these tests were evaluated and scored daily for clinical signs of EAE.

The severity of EAE was scored according to the following criteria: grade 1-decreased tail tone: grade 2- a clumsy gait : grade 3- weakness of one or more limb: grade 4- paraplegia or hemiplegia.

The FR-900506 substance was dissolved in olive oil and administered orally for 19 days starting on day 0 (the day of first immunization). As shown in Table 15, the FR-900506 substance clearly prevented the development of clinical signs of EAE.

TABLE 15

Effect of FR-900506 Substance on Experimental Allergic Encephalomyelitis in SJL/J Mice

| | Dose (mg/kg) | Number of Animals with Disease at Day 24 |
|---|---|---|
| Control (olive oil) | — | 10/10 |
| FR-900506 Substance | 32 | 0/5 |

Test 6

Effect of Tricyclo Compounds (I) on Local Graft-versus-Host Reaction (GvHR) in Mice The viable spleen cells ($1 \times 10^7$ cells) from C57BL/6 donors were injected subcutaneously into the right hind foot pad of BDF$_1$ mice to induce local GvHR. The mice were killed 7 days later and both right (injected paw) and left (uninjected paw) popliteal lymph nodes (PLN) were weighed The GvHR was expressed as the weight difference between right and left PLN.

The FR-900506 substance was dissolved in olive oil and administered orally for five days starting on the same day as sensitization.

ED$_{50}$ Value of the FR-900506 substance for prevention of the local graft-versus-host reaction was 19 mg/kg.

Test 7

Acute toxicities of Tricyclo Compounds (I)

Test on acute toxicities of the FR-900506, FR-900520, FR-900523 and FR-900525 substances in ddY mice by intraperitoneal injection were conducted, and the dead at dose of 100 mg/kg could not be observed in each case.

Test 8

Effect of Tricyclo Compounds (I) on Antibody Formation in mice (Assay for the haemagglutination test)

Male BDF$_1$ mice 6 to 8 weeks of age were used for this test. The mice were immunized on day 0 with $1 \times 10^8$ sheep erythrocytes (SRBC) intraperitoneally. Serum aggulutinin titers were determined for each individual animal with sedimentation of erythrocytes by serial two fold dilutions. The titers are expressed as $-\log_2$.

The FR-900506 substance was administered orally for 5 days from one day before immunization to day 3.

The results of each experiments were evaluated by means of Student's t-test as shown in Table 16.

TABLE 16

Effect of FR-900506 Substance on antibody formation in mice

| | Dose (mg/kg) | Number of Animals | Haemagglutination Mean log$_2$ titer ± SE | ED$_{50}$ (mg/kg) |
|---|---|---|---|---|
| Control | — | 5 | 8.2 ± 0.2 | — |
| FR-900506 | 10 | 5 | 7.6 ± 0.4 | |
| | 32 | 5 | 6 0 ± 0.45 | 16.9 |
| | 100 | 5 | 4.4 ± 0.75 | |

Test 9

Effect of Tricyclo Compounds (I) on in vivo Plaque Forming Cell (PFC) Response in Mice Male C3H/He mice 6 to 7 weeks of age were used for this test. The mice were immunized on day 0 with 0.2 ml of $1 \times 10^8$ washed sheep erythrocytes intravenously. Spleens were removed on day 4 and spleen cells were incubated in the presence of SRBC as described by Cunningham and Szenberg (1968). Tests were evaluated by enumeration of direct generated plaque forming cells in the presence of complement. Suspensions of spleen cells were counted with a Microcellcounter CC-130 (Sysmex, Japan) and PFC results were calculated as PFC/$10^6$ recovered cells.

The FR-900506 substance was administered orally for 4 days starting from the immunization.

The results of each experiment were evaluated by means of Student's t-test as shown in Table 17.

TABLE 17

Effect of FR-900506 Substance on in vivo PFC Response in Mice

| | Dose (mg/kg) | Number of Animals | PFC/$10^6$ cells | ED$_{50}$ (mg/kg) |
|---|---|---|---|---|
| Control | — | 5 | 5054 ± 408 | — |
| FR-900506 | 3.2 | 5 | 3618 ± 476 | |
| | 10 | 5 | 1382 ± 243 | 5.9 |
| | 32 | 5 | 657 ± 41 | |
| | 100 | 5 | 278 ± 41 | |

Test 10

Effect of Tricyclo Compounds (I) on Contact-Delayed Hypersensitivity in mice Female ICR mice were used for this test. A tenth of a 7% (w/v) solution of picryl chloride in ethanol prepared at the time of the experiment was applied to the ventral surface of previously shaved animals. Such a sensitization was performed twice at intervals of 7 days. Seven days later, the thickness of the ears were measured with an ordinary engineer's micrometer and a 1% (w/v) solution of picryl chloride in olive oil was painted to both surfaces of each ear. The inflammation was evaluated 24 hours later by measuring the both of ears. The results were expressed as the average increase in thickness of the ears measured in units of $10^{-3}$ cm.

The FR-900506 substance was injected for 14 days orally, starting from the first sensitization.

Statistical significance was evaluated by Student's t-test as shown in Table 18.

TABLE 18

Effect of FR-900506 Substance on contact-delayed hypersensitivity in mice

| | Dose (mg/kg) | Number of Animals | Increase of ears at 24 hours after challenge ($\times 10^{-3}$ cm) |
|---|---|---|---|
| Control | — | 5 | 15.5 ± 0.8 |
| FR-900506 | 32 | 5 | 6 4 ± 1.6 |
| | 100 | 5 | 2.2 ± 1.5 |

Test 11

Effect of Tricyclo Compounds (I) on Delayed Type Hypersensitivity (DTH) Response to methylated bovine serum albumin (MBSA)

Female BDF1 mice were used for this test The mice were sensitized with a subcutaneous injection of 0.1 ml emulsion consisting of equal volume of MBSA (2 mg/ml) and Freund's incomplete adjuvant(FIA) Seven days later, a 0.05 ml challenge dose of 0.4 mg/ml MBSA in saline was injected into the plantar region of the right hind foot and 0.05 ml saline into the left hind foot to act as a control Twenty four hours after challenge, both hind feet were measured with a dial gauge and the mean challenge in footpad thickness was measured.

The FR-900506 substance was injected for 8 days orally, starting from the sensitization.

Statistical significance was evaluated by Student's t-test as shown in Table 19

TABLE 19

Effect of FR-900506 Substance on DTH to MBSA in mice

| | Dose (mg/kg) | Number of Animals | Footpad Swelling ($\times 10^{-3}$ cm) | $ED_{50}$ (mg/kg) |
|---|---|---|---|---|
| Control | — | 5 | 57.4 ± 3.4 | — |
| FR-900506 | 10 | 5 | 31.0 ± 4.4 | |
| | 32 | 5 | 20.8 ± 4.4 | 18.4 |
| | 100 | 5 | 7.8 ± 1.6 | |

Test 12

Inhibition of Interleukin-2 (IL-2) Production by Tricyclo Compounds (I)

The mixed lymphocyte reaction (MLR) was performed in microtiter plates, with each well containing $5 \times 10^5$ C57BL/6 responder cells ($H-2^b$), $5 \times 10^5$ mitomycin C treated (25 μg/ml mitomycin C at 37° C. for 30 minutes and washed three times with RPMI 1640 medium) BALB/C stimulator cells ($H-2^b$) in 0.2 ml RPMI 1640 medium supplemented with 10% fetal calf serum, 2mM sodium hydrogen carbonate, penicillin 20 (50 unites/ml) and streptomycin (50 μg/ml). The cells were incubated at 37° C in humidified atmosphere of 5% carbon dioxide and 95% of air for 48 hours and the supernatant was collected. The FR-900506 substance was dissolved in ethanol and further diluted in RPMI 1640 medium and added to the cultures to give final concentrations of 0.1 μg/ml or less.

The IL-2 activity was measured according to the method described by S. Gillis et. al. [Journal of Immunology, Vol. 120, page 2027, (1978)]. The IL-2 dependent CTLL-2 cell line was used to quantitate IL-2 activity Cells ($5 \times 10^3$/well) were cultured at 37° C. for 24 hours with various dilutions of IL-2 containing supernatant from MLR. The uptake of $^3$H-thymidine was measured by pulsing cultures with 0.5 μCi of $^3$H-thymidine for 6 hours. The unit value was calculated by dilution analysis of test sample and was compared with a laboratory standard preparation in which 100 units are equivalent to the amount of IL-2 necessary to achieve 50% proliferation of CTLL-2 cells.

As shown in Table 20, the FR-900506 substance of the present invention inhibited the production of IL-2 from mouse MLR.

TABLE 20

Effect of the FR-900506 Substance on IL-2 Production

| FR-900506 concentration (nM) | IL-2 (units/ml) | Inhibition % |
|---|---|---|
| 10 | 0 | 100 |
| 1 | 0 | 100 |
| 0.3 | 0.2 | 99.5 |
| 0.1 | 25.0 | 34.4 |
| 0 | 38.1 | — |

The FR-900506 substance also inhibited lymphokine production such as interleukin 3 and interferones, especially γ-interferone, in the supernatant of MLR.

The pharmaceutical composition of this invention can be used in the form of a pharmaceutical preparation, for example, in solid, semisolid or liquid form, which contains the tricyclo compounds (I) of the present invention, as an active ingredient, in admixture with an organic or inorganic carrier or excipient suitable for external, enteral or parenteral applications The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to human, it is preferable to apply it by parenteral or enteral administration. While the dosage of therapeutically effective amount of the tricyclo compounds (I) varies from and also depends upon the age and condition of each individual patient to be treated, a daily dose of about 0.01–1000 mg, preferably 0.1–500 mg and more preferably 0.5–100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples are given for the purpose of illustrating the present invention.

EXAMPLE 1

Isolation of *Streptomyces tsukubaensis* No. 9993

*Streptomyces tsukubaensis* No. 9993 was isolated by using dilution plate techniques as shown in the following.

About one gram soil which was collected at Toyosato-cho, Tsukuba Gun, Ibaraki Prefecture, Japan, was added to a sterile test tube and the volume made up to 5 ml with sterile water. The mixture was then blended for 10 second by a tube buzzer and kept on 10 minutes. The supernatant was sequentially diluted by 100 fold with sterile water. The diluted solution (0.1 ml) was spread on Czapek agar supplemented with thiamine hydrochloride (saccharose 30 g, sodium nitrate 3 g, dipotassium phosphate 1 g, magnesium sulfate 0.5 g, potassium chloride 0.5 g, ferrous sulfate 0.01 g, thiamine hydrochloride 0.1 g, agar 20 g, tap water 1000 ml; pH 7.2) in a Petri dish. The growing colonies developed on the plates after 21 days incubation at 30° C. were transferred to slants [yeast-malt extract agar (ISP-medium 2)], and cultured for 10 days at 30° C. Among of the colonies isolated, the *Streptomyces tsukubaensis* No. 9993 could be found.

Fermentation

A culture medium (160 ml) containing glycerin (1%), soluble starch (1 %), glucose (0.5%), cottonseed meal (0.5%), dried yeast (0.5%), corn steep liquor (0.5%) and calcium carbonate (0.2%) (adjusted to pH 6.5) was poured into each of twenty 500 ml-Erlenmeyer flasks and sterilized at 120° C. for 30 minutes. A loopful of slant culture of *Streptomyces tsukubaensis* No.9993, FERM BP-927 was inoculated to each of the media and cultured at 30° C. for 4 days on a rotary shaker. The resultant culture was inoculated to a medium containing soluble starch (4.5%), corn steep liquor (1%), dried yeast (1%), calcium carbonate (0.1%) and Adekanol (defoaming agent, Trade Mark, maker; Asahi Denka Co ) (0.1%) (150 liters) in a 200-liter jar-fermentor, which had been sterilized at 120° C. for 20 minutes in advance, and cultured at 30° C. for 4 days under aeration of 150 liters/minutes and agitation of 250 rpm.

Isolation and Purification

The cultured broth thus obtained was filtered with an aid of diatomaseous earth (5 kg). The mycelial cake was extracted with methanol (50 liters), yielding 50 liters of the extract. The methanol extract from mycelium and the filtrate were combined and passed through a column of a non-ionic adsorption resin "Diaion HP-20" (Trade Mark, maker Mitsubishi Chemical Industries Ltd.)( 10 liters). After washing with water (30 liters) and aqueous methanol (30 liters), elution was carried out with methanol. The eluate was evaporated under reduced pressure to give residual water (2 liters) This residue was extracted with ethyl acetate (2 liters) The ethyl acetate extract was concentrated under reduced pressure to give an oily residue. The oily residue was mixed with twice weight of acidic silica gel special silica gel grade 12, maker Fuji Devison Co.), and this mixture was slurried in ethyl acetate After evaporating the solvent, the resultant dry powder was subjected to column chromatography of the same acid silica gel (800 ml) which was packed with n-hexane. The column was developed with n-hexane (3 liters), a mixture of n-hexane and ethyl acetate (9:1 v/v, 3 liters and 4:1 v/v, 3 liters) and ethyl acetate (3 liters). The fractions containing the object compound were collected and concentrated under reduced pressure to give an oily residue The oily residue was dissolved in a mixture of n-hexane and ethyl acetate (1:1 v/v, 30 ml) and subjected to column chromatography of silica gel (maker Merck Co., Ltd 230–400 mesh) (500 ml) packed with the same solvents system.

Elution was carried out with a mixture of n-hexane and ethyl acetate (1:1 v/v, 2 liters and 1:2 v/v, 1.5 liters). Fractions containing the first object compound were collected and concentrated under reduced pressure to give a yellowish oil The oily residue was mixed twice weight of acidic silica gel and this mixture was slurried in ethyl acetate. After evaporating the solvent, the resultant dry powder was chromatographed on acidic silica gel packed and developed with n-hexane Fractions containing the object compound were collected and concentrated under reduced pressure to give crude FR-900506 substance (1054 mg) in the form of white powder.

100 mg Of this crude product was subjected to high performance liquid chromatography. Elution was carried out using a column (8$\phi$×500 mm) with Lichrosorb SI 60 (Trade Mark, made by Merck & Co.) as a carrier This chromatography was monitored by UV detector at 230 nm and mobile phase was a mixture of methylene chloride and dioxane (85:15 v/v) under flow rate of 5 ml/minute., and the active fractions were collected and evaporated. This high performance chromatography was repeated again, and 14 mg of the purified FR-900506 substance was obtained as white powder.

Further, elution was continuously carried out with ethyl acetate (1.5 liters), and fractions containing the second object compound were collected and concentrated under reduced pressure to give crude FR-900525 substance (30 mg) in the form of yellowish oil.

EXAMPLE 2

Fermentation

A preculture medium (100 ml) containing glycerin (1%), corn starch (1%), glucose (0.5%), cottenseed meal (1%), corn steep liquor (0.5%), dried yeast (0 5%) and calcium carbonate (0.2%) at pH 6.5 was poured into a 500 ml-Erlenmeyer flask and sterilized at 120° C. for 30 minutes. A loopful of slant culture of *Streptomyces tsukubaensis* No. 9993 was inoculated to the medium and cultured at 30° C. for four days. The resultant culture was transferred to the same preculture medium (20 liters) in 30 liters jar-fermentor which had been sterilized at 120° C. for 30 minutes in advance After the culture was incubated at 30° C. for 2 days, 16 liters of the preculture was inoculated to a fermentation medium (1600 liters) containing soluble starch (4.5%), corn steep liquor (1%), dried yeast (1%), calcium carbonate (0.1%) and Adekanol (defoaming agent, Trade Mark, maker Asahi Denka Co.) (0.1%) at pH 6.8 in 2 ton tank which had been sterilized at 120° C. for 30 minutes in advance and cultured at 30° C. for 4 days.

Isolation and Purification

The cultured broth thus obtained was filtered with an aid of diatomaseous earth (25 kg). The mycelial cake was extracted with acetone (500 liters), yielding 500 liters of the extract. The acetone extract from mycelium and the filtrate (1350 liters) were combined and passed through a column of a non-ionic adsorption resin "Diaion HP-20" {Trade Mark, maker Mitsubishi Chemical Industries Ltd.) (100 liters). After washing with water (300 liters) and 50% aqueous acetone (300 liters), elution was carried out with 75% aqueous acetone. The eluate was evaporated under reduced pressure to give residual water (300 liters). This residue was extracted with ethyl acetate (20 liters) three times. The ethyl acetate extract was concentrated under reduced pressure to give an oily residue The oily residue was mixed with twice weight of acidic silica gel (special silica gel grade 12, maker Fuji Devison Co.), and this mixture was slurried in ethyl acetate. After evaporating the solvent, the resultant dry powder was subjected to column chromatography of the same acidic silica gel (8 liters) which was packed with n-hexane The column was developed with n-hexane (30 liters), a mixture of n-hexane and ethyl acetate (4:1 v/v, 30 liters) and ethyl acetate (30 liters). The fractions containing the object compound were collected and concentrated under reduced pressure to give an oily residue The oily residue was mixed with twice weight of acidic silica gel and this mixture was slurried in ethyl acetate. After evaporating the solvent, the resultant dry powder was rechromatographed on acidic silica gel (3.5 liters) packed with n-hexane The column was developed with n-hexane (10 liters), a mixture of n-hexane and ethyl acetate (4:1 v/v, 10 liters) and ethyl acetate (10 liters). Fractions containing the object compound were collected and concentrated under reduced pressure to give a yellowish oil. The oily residue was dissolved in a mixture of n-hexane and ethyl acetate (1 1 v/v, 300 ml) and subjected to column chromatography of silica gel (maker Merck Co., Ltd. 230–400 mesh) (2 liters) packed with the same solvents system. Elution was curried out with a mixture of n-hexane and ethyl acetate (1:1 v/v, 10 liters and 1:2 v/v 6 liters) and ethyl acetate (6 liters).

Fractions containing the first object compound were collected and concentrated under reduced pressure to give FR-900506 substance in the form of white powder (34 g). This white powder was dissolved in acetonitrile and concentrated under reduced pressure This concentrate was kept at 5° C. overnight and prisms (22.7 g) were obtained. Recrystallization from the same solvent gave purified FR-900506 substance (13.6 g) as colorless prisms.

Further, fractions containing the second object compound were collected and concentrated under reduced pressure to give crude FR-900525 substance (314 mg) in the form of yellowish powder.

EXAMPLE 3

Fermentation

A culture medium (160 ml) containing glycerin (1%), corn starch (1%), glucose (0.5%), cottonseed meal (1%), dried yeast (0.5%), corn steep liquor (0.5%) and calcium carbonate (0.2%) (adjusted to pH 6.5) was poured into each of ten 500 ml-Erlenmeyer flasks and sterilized at 120° C. for 30 minutes. A loopful of slant culture of Strectomyces tsukubaensis No. 9993 was inoculated to each of the medium and cultured at 30° C. for 4 days on a rotary shaker. The resultant culture was inoculated to a medium containing soluble starch (5%), peanut powder (0.5%), dried yeast (0.5%), gluten meal (0.5%), calcium carbonate (0.1%) and Adekanol (deforming agent, Trade Mark, maker Asasi Denka Co.) (0.1%) (150 liters) in a 200-liter jar-fermentor, which had been sterilized at 120° C. for 20 minutes in advance, and cultured at 30° C. for 4 days under aeration of 150 liters/minutes and agitation of 250 rpm.

Isolation and Purification

The cultured broth thus obtained was filtered with an aid of diatomaseous earth (5 kg). The mycelial cake was extracted with acetone (50 liters), yielding 50 liters of the extract. The acetone extract from mycelium and the filtrate (135 liters) were combined and passed through a column of a non-ionic adsorption resin "Diaion HP-20" (Trade Mark, maker Mitsubishi Chemical Industries Ltd.) (10 liters). After washing with water (30 liters) and 50% aqueous acetone (30 liters), elution was carried out with 75% aqueous acetone. The eluate (30 liters) was evaporated under reduced pressure to give residual water (2 liters). This residue was extracted with ethyl acetate (2 liters) three times. The ethyl acetate extract was concentrated under reduced pressure to give an oily residue The oily residue was mixed with twice weight of acidic silica gel (special silica gel grade 12, maker Fuji Devison Co ), and this mixture was slurried in ethyl acetate. After evaporating the solvent, the resultant dry powder was subjected to column chromatography of the same acidic silica gel (800 ml) which was packed with n-hexane The column was developed with n-hexane (3 liters), a mixture of n-hexane and ethyl acetate (4 1 v/v, 3 liters) and ethyl acetate (3 liters). The fractions containing the object compound were collected and concentrated under reduced pressure to give an oily residue. The oily residue was dissolved in a mixture of n-hexane and ethyl acetate (1:1 v/v, 30 ml) and subjected to column chromatography of silica gel (maker Merck Co., Ltd. 230–400 mesh) (500 ml) packed with the same solvents system. Elution was carried out with a mixture of n-hexane and ethyl acetate (1:1 v/v, 2 liters and 1:2 v/v, 1.5 liters) and ethyl acetate (1.5 liters).

Fractions containing the first object compound were collected and concentrated under reduced pressure to give crude FR-900506 substance (3 g) in the form of yellowish powder.

Further, fractions containing the second object compound were collected and concentrated under reduced pressure to give an oily residue This oily residue was rechromatographed with silica gel to give a yellowish oil. The oily residue was mixed with twice weight of acidic silica gel and this mixture was slurried in ethyl acetate. After evaporating the solvent, the resultant dry powder was chromatographed on acidic silica gel (100 ml) packed and developed with n-hexane Fractions containing the object compound were collected and concentrated under reduced pressure to give FR-900525 substance in the form of pale yellowish powder (380 mg) This powder was dissolved in a mixture of n-hexane and ethyl acetate (1:2 v/v, 5 ml) and subjected to acidic silica gel (special silica gel grade 922, maker Fuji Devison Co ) (100 ml) packed and washed with the same solvent system. Elution was carried out with ethyl acetate. The active fractions were collected and evaporated under reduced pressure to give the purified FR-900525 substance (230 mg) in the form of white powder.

EXAMPLE 4

Isolation of Streptomyces hygroscopicus subsp. yakushimaensis No. 7238

Streptomyces hygroscopicus subsp. yakushimaensis No. 7238 was isolated by using dilution plate techniques as shown in the following.

About one gram soil which was collected at Yakushima, Kagoshima Prefecture, Japan, was added to a sterile test tube and the volume made up to 5 ml with sterile water. The mixture was then blended for 10 seconds by a tube buzzer and kept on 10 minutes. The supernatant was sequentially diluted by 100 fold with sterile water. The diluted solution (0.1 ml) was spread on Czapek agar supplemented with thiamine hydrochloride (saccharose 30 g, sodium nitrate 3 g, dipotassium phosphate 1 g, magnesium sulfate 0.5 g, potassium chloride 0.5 g, ferrous sulfate 0.01 g, thiamine hydrochloride 0.1 g, agar 20 g, tap water 1000 ml; pH 7.2) in a Petri dish The growing colonies developed on the plates after 21 days incubation at 30° C. were transferred to slants [yeast-malt extract agar (ISP-medium 2)], and cultured for 10 days at 30° C. Among of the colonies isolated, the Streptomyces hygroscopicus subsp. yakushimaensis No. 7238 could be found

Fermentation

A culture medium (160 ml) containing glycerin (1%), soluble starch (1%), glucose (0.5%), cottonseed meal (0.5%), dried yeast (0.5%), corn steep liquor (0.5%) and calcium carbonate (0.2%) (adjusted to pH 6.5) was poured into each of twenty 500 ml-Erlenmeyer flasks and sterilized at 120° C. for 30 minutes A loopful of slant culture of *Streptomyces hygroscopicus* subsp. vakushimaensis No. 7238, FERM BP-928 was inoculated to each of the media and cultured at 30° C. for 4 days on a rotary shaker. The resultant culture was inoculated to a medium containing glucose (4 5%), corn steep liquor (1%), dried yeast (1%), gluten meal (1%), wheat germ (0.5%), calcium carbonate (0.1%) and Adekanol (defoaming agent, Trade Mark, maker Asahi Denka Co.) (0.1%) (150 liters) in a 200-liter jar-fermentor, which had been sterilized at 120° C. for 20 minutes in advance, and cultured at 30° C. for 4 days under aeration of 150 liters/minutes and agitation of 250 rpm.

Isolation and Purification

The cultured broth thus obtained was filtered with an aid of diatomaseous earth (5 kg). The mycelial cake was extracted with acetone (50 liters), yielding 50 liters of the extract The acetone extract from mycelium and the filtrate (135 liters) were combined and passed through a column of a non-ionic adsorption resin "Diaion HP-20" (Trade Mark, maker Mitsubishi Chemical Industries Ltd.)( 10 liters). After washing with water (30 liters) and aqueous acetone (30 liters), elution was carried out with acetone. The eluate was evaporated under reduced pressure to give residual water (2 liters). This residue was extracted with ethyl acetate (4 liters) The ethyl acetate extract was concentrated under reduced pressure to give an oily residue The oily residue was mixed with twice weight of acidic silica gel (special silica gel grade 12, maker Fuji Devison Co.), and this mixture was slurried in ethyl acetate. After evaporating the solvent, the resultant dry powder was subjected to column chromatography of the same acid silica gel (800 ml) which was packed with n-hexane The column was developed with n-hexane (3 liters), a mixture of n-hexane and ethyl acetate (4:1 v/v, 3 liters) and ethyl acetate (3 liters). The fractions containing the FR-900520 and FR-900523 substances were collected and concentrated under reduced pressure to give an oily residue The oily residue was dissolved in a mixture of n-hexane and ethyl acetate (1:1 v/v, 50 ml) and subjected to column chromatography of silica gel (maker Merck Co., Ltd. 70 - 230 mesh) (1000 ml) packed with the same solvents system. Elution was carried out with a mixture of n-hexane and ethyl acetate (1:1 v/v, 3 liters and 1:2 v/v, 3 liters) and ethyl acetate (3 liters). Fractions containing the object compounds were collected and concentrated under reduced pressure to give a yellowish powder (4.5 g). This powder was dissolved in methanol (20 ml) and mixed with water (10ml) The mixture was chromatographed on a reverse phase silica gel "YMC" (60-200 mesh) (500ml) (Trade Mark, maker Yamamura Chemical Institute) packed and developed with a mixture of methanol and water (4:1 v/v).

Fractions containing the FR-900520 substance were collected and concentrated under reduced pressure to give crude product of the FR-900520 substance (1.8 g) in the form of pale yellowish powder This powder was dissolved in a small amount of diethyl ether After standing overnight, the precipitated crystals were collected by filtration, washed with diethyl ether and then dried under reduced pressure Recrystallization from diethyl ether gave 600 mg of the purified FR-900520 substance in the form of colorless plates.

The chromatography of the reverse phase silica gel was carried on with the same solvents system, and the subsequent fractions containing the FR-900523 substance were collected and then concentrated under reduced pressure to give crude product of the FR-900523 substance (0.51 g) in the form of pale yellowish powder This crude product was dissolved in acetonitrile (3 ml) and subjected to a reverse phase silica gel "YMC" (70 ml) packed and developed with a mixture of acetonitrile, tetrahydrofuran and 50 mM phosphate buffer solution (pH 2.0) (3:2:5, v/v). Fractions containing the object compound were collected and were extracted with ethyl acetate. This extract was concentrated under reduced pressure to give a yellowish white powder (190 mg) The yellowish white powder was chromatographed again on a reverse phase silica gel "YMC" to give white powder (80 mg). This white powder was dissolved in a small amount of diethyl ether and allowed to stand overnight at room temperature to give 56mg of crystals Recrystallization from diethyl ether gave 34mg of the FR-900523 substance in the form of colorless needles.

EXAMPLE 5

To a solution of the FR-900506 substance (10.4 mg) in dichloromethane (0.2 ml) were added pyridine (0.1 ml) and acetic anhydride (0.05 ml) at room temperature, and the mixture was stirred for 5 hours. The solvent was removed from the reaction mixture under reduced pressure The residue was subjected to silica gel thin layer chromatography (developing solvent: diethyl ether and dichloromethane, 1:2 v/v) to give 12-[2-(4-acetoxy-3-methoxycyclohexyl)-1-methylvinyl]-17-allyl-1,14-dihydroxy23,25-dimethoxy-13,19,21,27-tetramethyl-11,28-dioxa-4-azatricyclo[22.3.1 .0$^{4,9}$]octacos-18-ene-2,3,10,16-tetraone (6.0 mg).

IR $\gamma(CHCl_3)$: 3520, 1728, 1705(sh), 1640, 1095 cm$^{-1}$

EXAMPLE 6

To a solution of the FR-900506 substance (52 5 mg) in dichloromethane (1 ml) were added pyridine (0.5 ml) and acetic anhydride (0.3 ml) at room temperature, and the mixture was stirred at room temperature for 9 hours. The solvent was removed from the reaction mixture under reduced pressure. The residue was subjected to silica gel thin layer chromatography (developing solvent diethyl ether and hexane, 3:1 v/v) to give 14-acetoxy-12-[2-(4-acetoxy-3-methoxycyclohexyl)-1-methylvinyl]-17-allyl-1-hydroxy-23,25-dimethoxy-13,19,21,27-tetramethyl-11,28-dioxa-4-azatricyclo[22.3.1.0$^{4,9}$]octacos-18-ene-2,3,10,16-tetraone (48.0 mg) and 12-[2-(4-acetoxy-3-methoxycyclohexyl)1-methylvinyl]-17-allyl-1-hydroxy-23,25-dimethoxy13,19,21,27-tetramethyl-11,28-dioxa-4-azatricyclo[22.3.1.0$^{4,9}$]octacosa-14,18-diene-2,3,10,16-tetraone (5.4 mg), respectively.

Former Compound

IR $\gamma(CHCl_3)$: 1730, 1720(sh), 1640 cm$^{-1}$

Latter Compound

IR $\gamma(CHCl_3)$: 1730, 1690, 1640, 1627 cm$^{-1}$

EXAMPLE 7

To a solution of the FR-900506 substance (9.7 mg) in dichloromethane (0.2 ml) and pyridine (0.1 ml) was added benzoyl chloride (50 μl) at room temperature, and the mixture was stirred at room temperature for 2 hours. The solvent was removed from the reaction mixture under reduced pressure to give a crude oil. This oil was purified on silica gel thin layer chromatography (developing solvent: diethyl ether and hexane, 2:1 v/v) to afford 17-allyl-12-[2-(4-benzoyloxy-3-methoxycyclohexyl)-1-methylvinyl]-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone (80.5 mg).

IR γ(CHCl$_3$): 3500, 1735(sh), 1710, 1640, 1600 cm$^{-1}$

EXAMPLE 8

To a solution of the FR-900506 substance (30.5 mg) in pyridine (1 ml) was added p-nitrobenzoyl chloride (ca. 100 mg), and the mixture was stirred at room temperature for 2 hours. The reaction mixture was diluted with ethyl acetate, and washed with a saturated aqueous sodium hydrogen carbonate, water 1N-hydrochloric acid, water, a saturated aqueous sodium hydrogen carbonate, water and an aqueous sodium chloride, successively, and then dried. The resulting solution was concentrated under reduced pressure, and the residue was purified on silica gel column chromatography to give 17-allyl-1,14-dihydroxy-23,25-dimethoxy-13,19,21,27-tetramethyl-12-[2-[4-(p-nitrobenzoyloxy)-3-methoxycyclohexyl]-1-methylvinyl]-11,28-dioxa-4-azatricyclo[22.3.1.0$^{4,9}$]octacos-18-ene-2,3,10,16-tetraone (37.7 mg).

IR γ(CHCl$_3$): 1720, 1640, 1610, 1530-1520 cm$^{-1}$

EXAMPLE 9

17-Allyl-1,14-dihydroxy-23,25-dimethoxy-13,19,21,27-tetramethyl-12-[2-[4-(3,5-dinitrobenzoyloxy)-3-methoxycyclohexyl]-1-methylvinyl]-11,28-dioxa-4-azatricyclo[22.3.1.0$^{4,9}$]octacos-18-ene-2,3,10,16-tetraone (36.0 mg) was obtained by reacting the FR-900506 substance (30.6 mg) with 3,5-dinitrobenzoyl chloride (33 mg) in pyridine (0.5 ml) in accordance with a similar manner to that of Example 8.

IR γ(CHCl$_3$): 1730, 1640, 1610, 1530-1520 cm$^{-1}$

EXAMPLE 10

17-Allyl-1,14-dihydroxy-23,25-dimethoxy-12-[2-[4-(2-l menthyloxyacetoxy)-3-methoxycyclohexyl]-1-methylvinyl]-13,19,21,27-tetramethyl-11,28-dioxa-4-azatricyclo[22.3.1.0$^{4,9}$ octacos-18-ene-2,3,10,16-tetraone (50.9 mg) was obtained by reacting the FR-900506 substance (48 mg) with 2-l-menthyloxyacetyl chloride (0.08 ml) in pyridine (0.5 ml) in accordance with a similar manner to that of Example 8.

IR γ(neat): 3520, 1760, 1740(sh), 1720(sh), 1652 cm$^{-1}$

EXAMPLE 11

To a solution of (-)-2-trifluoromethyl-2-methoxy-2-phenylacetic acid (51 mg) in ethyl acetate (10 ml) was added at room temperature N,N'-dicyclohexylcarbodiimide (47 mg). After stirring for 1.5 hours at room temperature, then the FR-900506 substance (25.0 mg) and 4-(N,N-dimethylamino)-pyridine (11 mg) were added, followed by stirring at room temperature for 3.5 hours. The resulting solution was concentrated to provide a residue, which was taken up in diethyl ether and then washed successively with hydrochloric acid, an aqueous sodium hydrogen carbonate and an aqueous sodium chloride. The organic layer was dried over sodium sulfate and concentrated to provide a residue, which was chromatographed on silica gel (developing solvent dichloromethane and diethyl ether, 10:1 v/v) to give 17-allyl-12-[2-[4-[(-)-2-trifluoromethyl-2-methoxy-2-phenylacetoxy]-3-methoxycyclohexyl]-1-methylvinyl]-1,14-dihydroxy-23,25-dimethoxy-13,19,21,27-tetramethyl-11,28-dioxa-4-azatricyclo[22.3.1.0$^{4,9}$ octacos-18-ene-2,3,10,16-tetraone (6.5 mg) and 17-allyl-14-[(-)-2-trifluoromethyl-2-methoxy-2-phenylacetoxy]-12-[2-[4-[(-)-2-trifluoromethyl-2-methoxy-2-phenylacetoxy]-3-methoxycyclohexyl]-1-methylvinyl]-1-hydroxy-23,25-dimethoxy-13,19,21,27-tetramethyl-11,28-dioxa-4-azatricyclo[22.3.1.0$^{4,9}$ ]octacos-18-ene-2,3,10,16-tetraone (20.2 mg).

Former Compound

IR γ(neat): 3510, 1750, 1730(sh), 1710, 1652, 1500 cm$^{-1}$ /

Latter Compound

IR γ(neat): 1750, 1720, 1652, 1500 cm$^{-1}$

EXAMPLE 12

To a stirred solution of the FR-900506 substance (248 mg) in pyridine (7 ml) were added succinic anhydride (145 mg) and 4-(N,N-dimethylamino)pyridine (7 mg), and the resulting mixture was stirred at room temperature for 18 hours. The reaction mixture was concentrated under reduced pressure and the residue was subjected to chromatography on silica gel (20 g) with ethyl acetate to give 17-allyl-12-[2-[4-(3-carboxypropionyloxy)-3-methoxycyclohexyl]-1-methylvinyl]-1,14-dihydroxy-23,25-dimethoxy-13,19,21,27-tetramethyl-11,28-dioxa-4-azatricyclo[22 3.1.0$^{4,9}$]octacos-18-ene-2,3,10,16-tetraone (90 mg).

IR γ(CHCl$_3$): 3500, 3100-2300, 1720, 1705(sh), 1635 cm$^{-1}$

EXAMPLE 13

To a solution of the FR-900506 substance (100.7 mg) in pyridine (3 ml) was added p-iodobenzenesulfonyl chloride (500 mg), and the mixture was stirred at room temperature for 36 hours. The solution was diluted with ethyl acetate and washed with a saturated aqueous sodium hydrogen carbonate, water and an aqueous sodium chloride. The organic layer was dried over sodium sulfate, filtered and concentrated under reduced pressure The residue was chromatographed on silica gel (developing solvent diethyl ether and hexane, 3:1 v/v) to give 17-allyl-1,14-dihydroxy-12-2-[4-(p-iodobenzenesulfonyloxy)-3-methoxycyclohexyl]-1-methylvinyl]-23,25-dimethoxy-13,19,21,27-tetramethyl-11,28-dioxa-4-azatricyclo[22.3.1.0$^{4,9}$ ]octacos-18-ene-2,3,10,16-tetraone (61 mg) and 17-allyl-1-hydroxy-12-[2-[4-(piodobenzenesulfonyloxy)-3-methoxycyclohexyl]-1-methylvinyl]-23,25-dimethoxy-13,19,21,27-tetramethyl-11,28-dioxa-4-azatricyclo[22.3.1.0$^{4,9}$]octacosa-14,18-diene-2,3,10,16-tetraone (12 mg), respectively.

Former Compound

IR γ(CHCl$_3$): 3470, 1730, 1717, 1692, 1635, 1568 cm$^{-1}$

Latter Compound

| $^1$H NMR δ ppm(CDCl$_3$): | 6.15 (d, J = 15Hz) | }1H) |
|---|---|---|
| | 6.25 (d, J = 15Hz) | |
| | 6.70 (dd, J = 15Hz, 10Hz) | }1H), |
| | 6.80 (dd, J = 15Hz, 10Hz) | |
| | 7.60 (2H, m), 7.90 (2H, m). | |

EXAMPLE 14

17-Allyl-12-[2-(4-d-camphorsulfonyloxy-3-methoxycyclohexyl)-1-methylvinyl]-1,14-dihydroxy-23,25-dimethoxy-13,19,21,27-tetramethyl-11,28-dioxa-4-azatricyclo[22.3.1$0^{4,9}$]octacos-18-ene-2,3,10,16-tetraone (34 mg) was obtained by reacting the FR-900506 substance (27 mg) with d-camphorsulfonyl chloride (97 mg) in pyridine (0.6 ml) in accordance with a similar manner to that of Example 13.

IR $\gamma$(neat): 3500, 1747, 1720(sh), 1710(sh), 1655 cm$^{-1}$

EXAMPLE 15

To a stirred solution of the FR-900506 substance (89.7 mg) in dichloromethane (3 ml) were added imidazole (118 mg) and tert-butyl-diphenylsilyl chloride (52.2 mg). After the mixture was stirred at room temperature for 2 hours, the reaction mixture was diluted with a saturated aqueous ammonium chloride and extracted three times with diethyl ether. The extract was washed with water and an aqueous sodium chloride, dried over sodium sulfate, and then concentrated under reduced pressure The residue was purified on silica gel column chromatography (developing solvent: ethyl acetate and hexane, 1:3 v/v) to give 17-allyl-12-[2-(4-tert-butyldiphenylsilyloxy-3-methoxycyclohexyl)-1-methylvinyl]-1,14-dihydroxy-2 ,25-dimethoxy-13,19,21,27-tetramethyl-11,28-dioxa-4-azatricyclo[22.3.1.$0^{4,9}$]octacos-18-ene-2,3,10,16-t traone (107 mg).

IR $\gamma$(neat): 3520, 1742, 1705, 1650 cm$^{-1}$

EXAMPLE 16

17-Allyl-12-[2-(4-tert-butyl-dimethylsilyloxy-3-methoxycyclohexyl)-1-methylvinyl]-1,14-dihydroxy-23,25-dimethoxy-13,19,21,27-tetramethyl-11,28-dioxa-4-azatricyclo[22.3.1.$0^{4,9}$]octacos-18-ene-2,3,10,16-tetraone (85 mg) was obtained by reacting the FR-900506 substance (80 mg) with tert-butyl-dimethylsilyl chloride (17 mg) in the presence of imidazole (15 mg) in N,N-dimethylformamide (1 ml) in accordance with a similar manner to that of Example 15.

IR $\gamma$(CHCl$_3$) : 1735, 1720(sh), 1700, 1640 cm$^{-1}$

EXAMPLE 17

To a solution of the FR-900506 substance (100 mg) in dimethyl sulfoxide (1.5 ml) was added acetic anhydride (1.5 ml), and the mixture was stirred at room temperature for 14 hours The reaction mixture was diluted with ethyl acetate and washed with a saturated aqueous sodium hydrogen carbonate, water and an aqueous sodium chloride. The organic layer was dried over sodium sulfate, filtered and then concentrated under reduced pressure The residue was subjected to thin layer chromatography on silica gel (developing solvent diethyl ether) to give 17-allyl-1,14-dihyroxy-23,25-dimethoxy-13,19,21,27-tetramethyl-12-[2-(4-methylthiomethoxy-3-methoxycyclohexyl)-1-methylvinyl]-11,28-dioxa-4-azatricyclo[22.3.1.04,9]octacosa-14,18-diene-2,3,10,16-tetraone (51 mg), 17-allyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.$0^{4,9}$]octacosa-14,18-diene-2,3,10,16-tetraone (18 mg) and 17-allyl-1,14-dihydroxy-23,25-dimethoxy-13,19,21,27-tetramethyl-12-[2-(4-methylthiomethoxy- 3-methoxycyclohexyl)-1-methylvinyl]-11,28-dioxa-4-azatricyclo[22.3.1.$0^{4,9}$]octacos-18-ene-2,3,10,16-tetraone (10 mg), respectively.

First Compound

IR $\gamma$(CHCl$_3$) : 3470, 1730, 1635, 1630(sh), 1580(sh) cm$^{-1}$

Second Compound

IR $\gamma$(CHCl$_3$) : 1728, 1640, 1090 cm$^{-1}$

Third Compound

IR $\gamma$(CHCl$_3$) : 3480, 1735, 1710, 1640 cm$^{-1}$

EXAMPLE 18

To a solution of 17-allyl-12-[2-(4-tert-butyl-dimethylsilyloxy-3-methoxycyclohexyl)-1-methylvinyl]-1,14-dihydroxy-23,25-dimethoxy-13,19,21,27-tetramethyl-11,28-dioxa-4-azatricyclo[22.3.1 9 octacos-18-ene-2,3,10,16-tetraone (39.9 mg) in pyridine (1.5 ml) was added acetic anhydride (0.5 ml}, and the mixture was stirred at room temperature for 6 hours. The solvent was removed from the reaction mixture under reduced pressure to give a crude oil, which was purified on silica gel thin layer chromatography (developing solvent: diethyl ether and hexane, 1:1 v/v) to afford 14-acetoxy-17-allyl-12-[2-(4-tert-butyl-dimethylsilyloxy-3-methoxycyclohexyl)-1-methylvinyl]-1-hydroxy-23,25-dimethoxy-13,19,21,27-tetramethyl-11,28-dioxa-4-azatricyclo[22.3.1.$0^{4,9}$]octacos-18-ene-2,3,10,16-tetraone (26 5 mg).

IR $\gamma$(CHCl$_3$) : 1728, 1715(sh), 1635 cm$^{-1}$

EXAMPLE 19

14-Acetoxy-17-allyl-12-[2-(4-tert-butyl-diphenylsilyloxy-3-methoxycyclohexyl)-1-methylvinyl]-1-hydroxy-23,25-dimethoxy-13,19,21,27-tetramethyl-11,28-dioxa-4-azatricyclo[22 3.1.$0^{4,9}$]octacos-18-ene-2,3,10,16-tetraone (10 mg) was obtained by reacting 17-allyl-12-[2-(4-tert-butyl-diphenylsilyloxy-3-methoxycyclohexyl)-1-methylvinyl]-1,14-dihydroxy-23,25-dimethoxy-13,19,21,27-tetramethyl-11,28-dioxa-4-azatricyclo[22.3.1.$0^{4,9}$ ]octacos-18-ene-2,3,10,16-tetraone (10.6 mg) with acetic anhydride (0.1 mg) in pyridine (0.2 ml) in accordance with a similar manner to that of Example 18.

IR $\gamma$(CHCl$_3$): 3500, 1730, 1720(sh), 1660(sh), 1640, 1620(sh), 1100 cm$^{-1}$

EXAMPLE 20

To a solution of 14-acetoxy-17-allyl-12-[2-(4-tert-butyl-diphenylsilyloxy-3-methoxycyclohexyl)-1-methylvinyl]-1-hydroxy-23,25-dimethoxy-13,19,21,27-tetramethyl-11,28-dioxa-4-azatricyclo[22.3.1.$0^{4,9}$]octacos-18-ene-2,3,10,16-tetraone (43.8 mg) in tetrahydrofuran (1.5 ml) was added potassium carbonate (ca 100 mg) at room temperature and the mixture was stirred at the same temperature for 3 hours. The reaction mixture was diluted with diethyl ether and the resulting solution was washed with a saturated aqueous ammonium chloride, water and an aqueous sodium chloride successively, and dried over sodium sulfate. The resulting solution was concentrated under reduced pressure and the residue was purified on silica gel thin layer chromatography (developing solvent: diethyl ether and hexane, 3:2 v/v) to give 17-allyl-12-[2-(4-tert-butyl-d iphenylsilyloxy-3-methoxycyclohexyl)-1-methylvinyl]-1-hydroxy-23,25-dimethoxy-13,19,21,27-tetramethyl-11,28-dioxa-4-azatricyclo[22.3.1.$0^{4,9}$]octacosa-14,18-diene-2,3,10,16-tetraone (30 mg).

IR $\gamma$(CHCl$_3$) : 1733, 1720(sh), 1685, 1640(sh), 1620 cm$^{-1}$

EXAMPLE 21

A solution of the FR-900506 substance (50 mg) in ethyl acetate (2 ml) was subjected to catalytic reduction using 10% palladium on carbon (10 mg) under atmospheric pressure at room temperature for 20 minutes. The reaction mixture was filtered and the filtrate was evaporated to dryness, which was purified on thin layer chromatography Development with a mixture of chloroform and acetone (5:1 v/v) gave 1,14-dihydroxy-12-[2-(4-hydroxy-3-methoxycyclohexyl)-1-methylvinyl]-23,25-dimethoxy-13,19,21,27-tetramethyl-17-propyl-11,28-dioxa-4-azatricyclo[22.3.1.04,9] octacos-18-ene-2,3,10,16-tetraone (50.0 mg).

IR γ(CHCl$_3$) : 3480, 1735(sh), 1717, 1700, 1650(sh), 1625 cm$^{-1}$

EXAMPLE 22

White powder of crude FR-900506 substance (1 g) obtained by a similar fermentation process to Example 1 was dissolved in acetonitrile (5 ml) and subjected to high performance liquid chromatography (HPLC) using Shimazu LC4A (Trade Mark, made by Shimazu Seisaku-sho). Steel column (25 mm inside diameter, 250 mm length) packed with YMC-S343 (ODS) (Trade Mark, made by Shimakyu Co., Ltd.) was used at a flow rate of 12 ml/min. Mobile phase was an aqueous mixture of 28% acetonitrile, 10% n-butanol, 0.075% phosphoric acid, 3.75 mM sodium dodecyl sulfate (SDS) and detection was carried out using Hitachi UV-recorder at 210 nm. One hundred μl of the sample was injected each time and the HPLC was repeated 50 times so that all the sample could be subjected to the column Each eluate with a retention time of 85 min. to 90 min. was collected and extracted with an equal volume of ethyl acetate (3.6 liters). The ethyl acetate layer was separated and washed with an aqueous sodium hydrogen carbonate (1%, 2 liters) and concentrated in vacuo to a small amount. SDS crystallized on concentration was removed by filtration. Crude powder obtained was dissolved in acetonitrile at a concentration of 100 mg/ml and applied again to HPLC. Mobile phase was an aqueous mixture of 12.5% acetonitrile, 9.75% n-butanol, 0.075% phosphoric acid, 3.75 mM SDS. The column was eluted at a flow rate of 10 ml/min. The eluates with a retention time of 131 min. to 143 min. were collected and extracted with equal volume of ethyl acetate The solvent layer was separated and washed with 1% aqueous sodium hydrogen carbonate and concentrated in vacuo to a small volume. SDS crystallized on concentration was removed by filtration.

Crude powder thus obtained was dissolved in a small amount of ethyl acetate and subjected to column chromatography using silica gel (10 ml) (Kiesel gel, 230–400 mesh, maker: Merck Co., Ltd.). The column was washed with a mixture of n-hexane and ethyl acetate (30 ml) (1:1 v/v) and a mixture of n-hexane and ethyl acetate (60 ml) (1:2 v/v). Elution was carried out using ethyl acetate and fractionated (each fraction : 3 ml). Fractions 18 to 24 were collected and concentrated in vacuo to dryness to give FR-900520 substance (24 mg).

EXAMPLE 23

A solution of the FR-900506 substance (310 mg), 2-trimethylsilylethyl 4-isocyanatobutyrate (350 mg) and triethylamine (6 drops) in anhydrous benzene (4 ml) was heated at 50° C. with stirring for 2 hours. The reaction mixture was allowed to stand at room temperature overnight. The mixture was concentrated to dryness under reduced processure to leave a residue, which was chromatographed on silica gel in chloroform. Elution was carried out with chloroform to give 17-allyl-12-[2-[3-methoxy-4-{3-(2-trimethylsilylethoxycarbonyl) propylcarbamoyloxy}cyclohexyl]-1-methylvinyl]-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone (99 mg). This product was treated with tetra(n-butyl)ammonium fluoride (0.12 m mole) in tetrahydrofuran (2.5 ml) at room temperature for 20 minutes. The reaction mixture was concentrated to dryness under reduced pressure to leave a residue, which was purified with preparative thin layer chromatography on silica gel. Elution with a mixture of chloroform and methanol (5:1) gave 17-allyl-12-[2-{4-(3-carboxypropylcarbamoyloxy)-3methoxycyclohexyl}-1-methylvinyl]-1,14-dihydroxy-23,25-dimethoxy-13,19,21,27-tetramethyl-11,28-dioxa-4-azatricyclo-[22.3.1.04,9]octacos-18-ene-2,3,10,16-tetraone (18.1 mg).

IR γ(CHCl$_3$) : 3550–3100, 2870, 2750–2400, 1730, 1690, 1630 cm$^{-1}$

What we claim is:

1. A method for treating resistance to transplantation which comprises administering an effective amount of a compound of the formula:

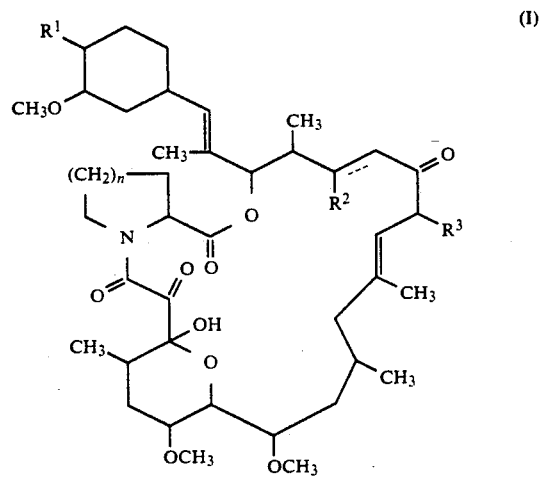

wherein
R$^1$ is hydroxy or pharmaceutically acceptable protected hydroxy selected from the group consisting of 1-(lower alkylthio)(lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy, and pharmaceutically acceptable organic carbamic acyloxy, R$^2$ is hydrogen or the same meanings as R$^1$, R$^3$ is methyl, ethyl, propyl or allyl, n is an integer of 1 or 2, and the symbol of a line and dotted line is a single bond or a double bond, or pharmaceutically acceptable basic salt thereof to a subject in need of said treatment.

2. A method for treating autoimmune disease which comprises administering an effective amount of a compound of the formula:

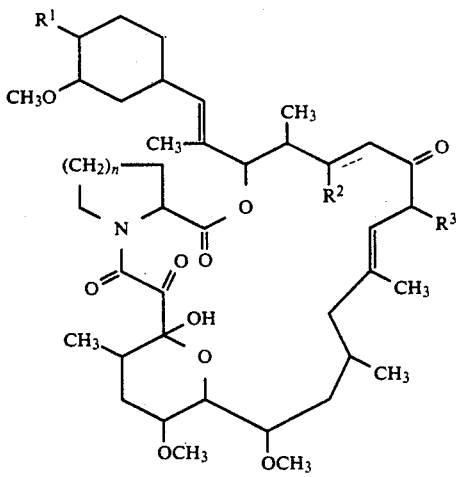

wherein
- R¹ is hydroxy or pharmaceutically acceptable protected hydroxyl selected from the group consisting of 1-(lower alkylthio)(lower)alkyloxy, tri(lower)alkylsilyloxy, lower alkyl-diphenyl-siloyloxy, pharmaceutically acceptable organic carboxylic acyloxy, pharmaceutically acceptable organic sulfonic acyloxy, and pharmaceutically acceptable organic carbamic acyloxy,
- R² is hydrogen or the same meanings as R¹,
- R³ is methyl, ehtyl, propyl or allyl,
- n is an integer of 1 to 2, and
- the symbol of a line and dotted line is a single bond or a double bond, or pharmaceutically acceptable basic salt thereof to a subject in need of said treatment.

3. A method for treating infectious diseases which comprises administering an effective amount of a compound of the formula (I)

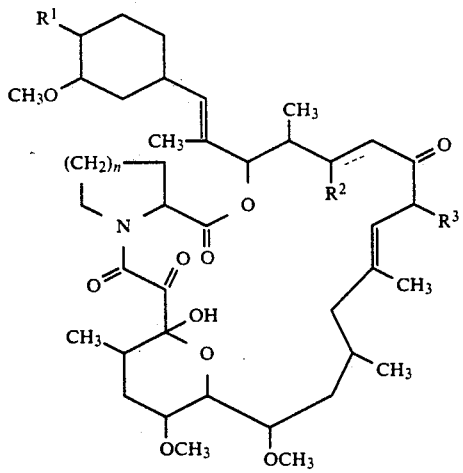

wherein
R¹ is hydroxy or pharmaceutically acceptable protected hydroxy selected from the group consisting of 1-(lower alkylthio)(lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy, and pharmaceutically acceptable organic carbamic acyloxy, R² is hydrogen or the same meanings as R¹,
R³ is methyl, ethyl, propyl or allyl,
n is an integer of 1 or 2, and
The symbol of a line and dotted line is a single bond or a double bond,
provided that when R¹ and R² are each hydroxy, n is an integer of 2 and the symbol of a line and dotted line is a single bond, then R³ is methyl, propyl or allyl, or pharmaceutically acceptable basic salt thereof to a subject in need of said treatment.

4. A method for treatment of diseases beneficially treated by external administration of compounds having immunosuppressive activity in a patient in need of such treatment, which comprises externally administering to such patient a compound of the formula:

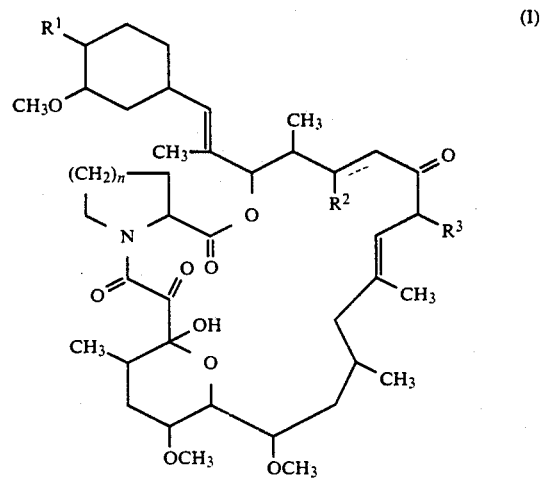

wherein
R¹ hydroxy or pharmaceutically acceptable protected hydroxy selected from the consisting of 1-(lower alkylthio)(lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy and pharmaceutically acceptable organic carbamic acyloxy, R² is hydrogen or the same meanings as R¹,
R³ is methyl, ethyl, propyl or allyl,
n is an integer of 1 or 2, and the symbol of a line and dotted line is a single bond or a double bond, or pharmaceutically acceptable basic salt thereof.

5. A method of treatment for treatment of diseases beneficially treated by administration of compounds having immunosuppressive activity in a patient in need of such treatment, which comprises administering to such patient a compound of the formula:

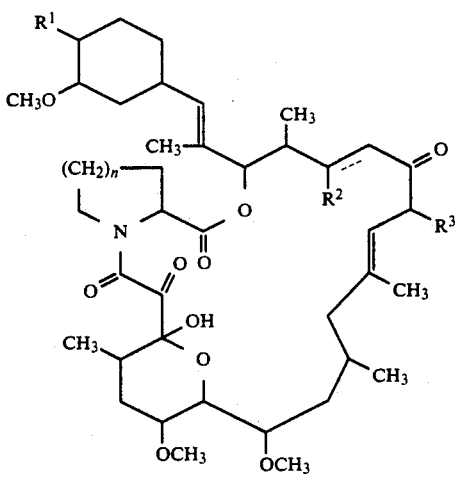

(I)

wherein
- R¹ is hydroxy or pharmaceutically acceptable protected hydroxy selected from the group consisting 1-(lower alkylthio)(lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy, and pharmaceutically acceptable organic carbamic acyloxy,
- R² is hydrogen or the same meanings as R¹,
- R³ is methyl, ethyl, propyl or allyl,
- n is an integer of 1 or 2, and the symbol of a line and dotted line is a single bond or a double bond, or pharmaceutically acceptable basic salt thereof.

6. A method of treating diseases exhibiting delayed type hypersensitivity by external application of an effective amount of a compound of the formula:

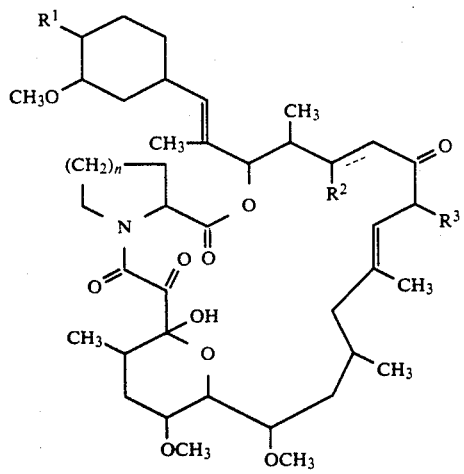

(I)

wherein
- R¹ is hydroxy or pharmaceutically acceptable protected hydroxy selected from the group consisting 1-(lower alkylthio)(lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy, and pharmaceutically acceptable organic carbamic acyloxy,
- R² is hydrogen or the same meanings as R¹,
- R³ is methyl, ethyl, propyl or allyl,
- n is an integer of 1 or 2, and the symbol of a line and dotted line is a single bond or a double bond, or pharmaceutically acceptable basic salt thereof to a subject in need of said treatment.

7. A method of treating lupus erythematosus which comprises the external application of an effective amount of a compound of the formula:

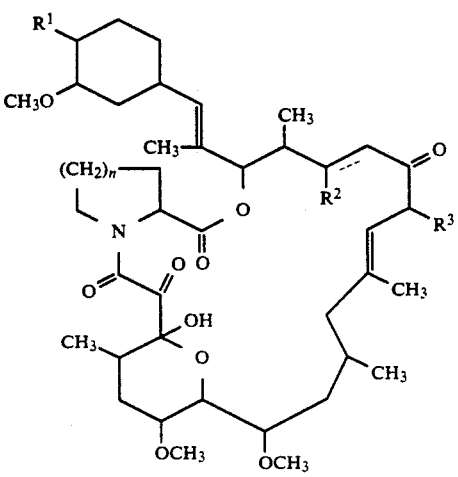

(I)

wherein
- R¹ is hydroxy or pharmaceutically acceptable protected hydroxy selected from the group consisting 1-(lower alkylthio)(lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy, and pharmaceutically acceptable organic carbamic acyloxy,
- R² is hydrogen or the same meanings as R¹,
- R³ is methyl, ethyl, propyl or allyl,
- n is an integer of 1 or 2, and the symbol of a line and dotted line is a single bond or a double bond, or pharmaceutically acceptable basic salt thereof to a subject in need of said treatment.

8. A method of treating autoimmune diseases by the external application of an effective amount of a compound of the formula:

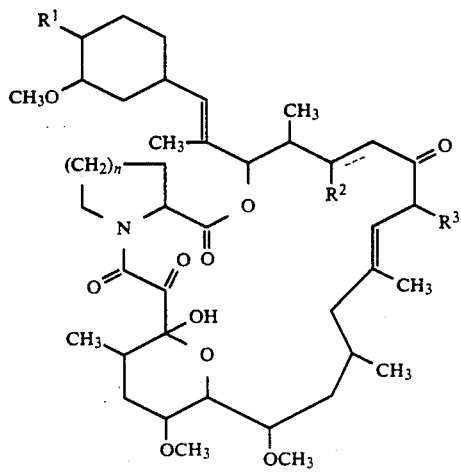

(I)

wherein $R^1$ is hydroxy or pharmaceutically acceptable protected hydroxy selected from the group consisting 1-(lower alkylthio)(lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy, and pharmaceutically acceptable organic carbamic acyloxy, $R^2$ is hydrogen or the same meanings as $R^1$, $R^3$ is methyl, ethyl, propyl or allyl, n is an integer of 1 or 2, and the symbol of a line and dotted line is a single bond or a double bond, or pharmaceutically acceptable basic salt thereof to a subject in need of said treatment.

9. A method for treating graft-versus-host diseases by medulla ossium transplantation which comprises administering an effective amount of a compound of the formula:

(I)

wherein
$R^1$ is hydroxy or pharmaceutically acceptable protected hydroxy selected from the group consisting 1-(lower alkylthio)(lower)alkyloxy, tri(lower)alkylsilyloxy, lower alkyl-diphenyl-silyloxy, pharmaceutically acceptable organic carboxylic acyloxy, pharmaceutically acceptable organic sulfonic acyloxy, and pharmaceutically acceptable organic carbamic acyloxy,
$R^2$ is hydrogen or the same meanings as $R^1$,
$R^3$ is methyl, ethyl, propyl or allyl,
n is an integer of 1 or 2, and the symbol of a line and dotted line is a single bond or a double bond, or pharmaceutically acceptable basic salt thereof to a subject in need of said treatment.

10. The method of any one of claim 1-9 which $R^1$ is hydroxy, $C_1$-$C_4$ alkanoyloxy which may have carboxy, cyclo ($C_5$-$C_6$)alkyloxy($C_1$-$C_4$) alkanoyloxy having two ($C_1$-$C_4$) alkyl groups on the cycloalkyl moiety, camphorsulfonyloxy, carboxy ($C_1$-$C_4$)-alkylcarboamoyloxy, tri($C_1$-$C_4$)alkylsily-($C_1$-$C_4$) alkoxycarbonyl($C_1$-$C_4$)alkylcarbamoyloxy, benzoyloxy which may have one or two nitro, benzenesulfonyloxy having halogen, or phenyl($C_1$-$C_4$)alkanoyloxy having $C_1$-$C_4$ alkoxy and trihalo($C_1$-$C_4$)alkyl, and
$R^2$ is hydrogen, hydroxy or $C_1$-$C_4$ alkanoyloxy.

11. The method of claim 10, in which n is an integer of 2.

12. The method of claim 11, in which the symbol of a line and dotted line is a single bond.

13. The method of claim 12, in which $R^1$ and $R^2$ are each hydroxy.

14. The method of claim 13, in which the compound is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

* * * * *

UNITED STATES PATENT AND TRADEMARK OFFICE
CERTIFICATE OF CORRECTION

PATENT NO. : 5,254,562

DATED : OCTOBER 19, 1993

INVENTOR(S) : MASAKUNI OKUHARA et al

It is certified that error appears in the above-identified patent and that said Letters Patent is hereby corrected as shown below:

Column 1, line 29, "a novel tricyclo compounds" should read --novel tricyclo compounds--;
       line 54, "substances In" should read --substances. In--.

Column 12, line 24 "Nakamura Therefore" should read --Nakamura. Therefore--;
       line 28, "IFO 12891 As a" should read --IFO 12891. As a--;
       line 30, "IFO 12891 Therefore, the strain" should read --IFO 12891. Therefore, the strain--.

Column 13, line 52, "of ways Agitation may be" should read --of ways. Agitation may be--.

Column 14, line 25, "C: 64.72%; H: 8.78%; N: 1.59%; 64.59%; 8.74%; 1.62%." should read --C: 64.72%, 64.59%; H: 8.78%, 8/74%; N: 1.59%, 1.62%.--;
       line 28, "Positive cerium" should read --Positive: cerium--;
       line 41, "Absorption Spectrum" should read --Absorption Spectrum:--.

UNITED STATES PATENT AND TRADEMARK OFFICE
CERTIFICATE OF CORRECTION

PATENT NO. : 5,254,562
DATED : OCTOBER 19, 1993
INVENTOR(S) : MASAKUNI OKUHARA et al

It is certified that error appears in the above-identified patent and that said Letters Patent is hereby corrected as shown below:

Column 14, line 48, "Resonance Spectrum" should read --Resonance Spectrum:--.

Column 15, line 21,

"

| Stationary Phase | Developing Solvent | Rf Values |
|---|---|---|
| silica gel plate | chloroform :methanol (10:1, v/v) | 0.58 |
| | ethyl acetate | 0.52 |
| (12) Property of the Substance: nuetral substance | | |

"

should read

--

| Stationary Phase | Developing Solvent | Rf Values |
|---|---|---|
| silica gel plate | chloroform :methanol (10:1, v/v) | 0.58 |
| | ethyl acetate | 0.52 |

(12) Property of the Substance: neutral substance--;
line 47, "C: 64.30%; H: 8.92%; N: 1.77%; 64.20%; 8.86%; 1.72%." should read --C: 64.30%, 64.20%; H: 8.92%, 8.86%; N: 1.77%, 17.2%.--.

Column 16, line 24, "conditions. From the above" should read --conditions.
From the above--.

UNITED STATES PATENT AND TRADEMARK OFFICE
CERTIFICATE OF CORRECTION

PATENT NO. : 5,254,562

DATED : OCTOBER 19, 1993

INVENTOR(S) : MASAKUNI OKUHARA et al

It is certified that error appears in the above-identified patent and that said Letters Patent is hereby corrected as shown below:

Column 17, line 6, ":-88 + (c=1.0 CHCl$_3$)" should read --:-88° (c=1.0 CHCl$_3$)--;

lines 38-39,

"
$$\begin{Bmatrix} 30.80 (t) \\ 30.66 (t) \end{Bmatrix} \quad \begin{Bmatrix} 28.60 (t) \end{Bmatrix} \quad \begin{matrix} 26.03 (d) \\ 26.98 (d) \end{matrix}$$

$$\begin{Bmatrix} 25.43 (t) \\ 24.40 (t) \end{Bmatrix} \quad \begin{Bmatrix} 18.93 (q) \\ 20.57 (q) \end{Bmatrix} \quad \begin{Bmatrix} 14.09 (q) \\ 13.95 (q) \end{Bmatrix}$$
"

should read

--
$$\begin{Bmatrix} 30.80 (t) \\ 30.66 (t) \end{Bmatrix} \quad \begin{Bmatrix} 28.60 (t) \end{Bmatrix} \quad \begin{matrix} 26.03 (d) \\ 26.98 (d) \end{matrix}$$

$$\begin{Bmatrix} 25.43 (t) \\ 24.40 (t) \end{Bmatrix} \quad \begin{Bmatrix} 18.93 (q) \\ 20.57 (q) \end{Bmatrix} \quad \begin{Bmatrix} 14.09 (q) \\ 13.95 (q) \end{Bmatrix}$$
--;

line 55, "(12) Property of the Substance: neutral substance" delete in its entirety.

UNITED STATES PATENT AND TRADEMARK OFFICE
CERTIFICATE OF CORRECTION

PATENT NO. : 5,254,562

DATED : OCTOBER 19, 1993

INVENTOR(S) : MASAKUNI OKUHARA et al

It is certified that error appears in the above-identified patent and that said Letters Patent is hereby corrected as shown below:

Column 17, line 56, "Property of the Substance" should read --Property of the Substance:--.

Column 18, line 30, "[21.3.1.04,8 heptacos" should read --21.3.1.0$^{4,8}$]heptacos--.

Column 19, line 6, "Gottlieb Methods for" should read --Gottlieb: Methods for--;
line 61, "agar Surface" should read --agar. Surface--.

Column 20, line 63, "No 7238" should read --No. 7238--;
line 64, "acid Accordingly" should read --acid. Accordingly--.

Column 21, line 1, "mentioned above The" should read --mentioned above. The--;
line 8, "were positive No" should read --were positive. No--;
line 27, "7%<,<10% 7%<,<10% 5%<,<%" should read --7%<,<10% 7%<,<10% 5%<,<7%--.

UNITED STATES PATENT AND TRADEMARK OFFICE
CERTIFICATE OF CORRECTION

PATENT NO. : 5,254,562
DATED : OCTOBER 19, 1993
INVENTOR(S) : MASAKUNI OKUHARA et al

It is certified that error appears in the above-identified patent and that said Letters Patent is hereby corrected as shown below:

Column 22, line 50, "can nbt utilize" should read --can not utilize--.

Column 23, line 36, "for use When" should read --for use. When--;

line 48, "therefor For" should read --therefor. For--;

line 49, "is employed Furthermore" should read --is employed. Furthermore--.

Column 25, lines 7-8,

"

| $\delta$ (ppm, CDCl$_3$): | 213.04 (s), | { 196.21 (s)<br>{ 193.23 (s), | { 169.07 (s)<br>{ 168.85 (s), |
|---|---|---|---|
| | 164.92 (s)<br>165.97 (s), | { 138.67 (s)<br>{ 139.53 (s), | { 132.46 (s)<br>{ 131.98 (s). |

"

should read --

| $\delta$ (ppm, CDCl$_3$): | 213.04 (s), | { 196.21 (s)<br>{ 193.23 (s), | { 169.07 (s)<br>{ 168.85 (s), |
|---|---|---|---|
| | { 164.92 (s)<br>{ 165.97 (s), | { 138.67 (s)<br>{ 139.53 (s), | { 132.46 (s)<br>{ 131.98 (s), |

--.

UNITED STATES PATENT AND TRADEMARK OFFICE
CERTIFICATE OF CORRECTION

PATENT NO. : 5,254,562

DATED : OCTOBER 19, 1993

INVENTOR(S) : MASAKUNI OKUHARA et al

It is certified that error appears in the above-identified patent and that said Letters Patent is hereby corrected as shown below:

Column 25, lines 19-20,

"
$$\begin{cases} 70.11 \text{ (d)} \\ 69.21 \text{ (d)}. \end{cases} \begin{cases} 57.02 \text{ (q)}. \\ \end{cases} \begin{matrix} 56.60 \text{ (q)} \\ 57.43 \text{ (q)}. \end{matrix}$$
$$\begin{cases} 56.23 \text{ (q)} \\ 55.98 \text{ (q)}. \end{cases} \begin{cases} 56.72 \text{ (d)} \\ 52.91 \text{ (d)}. \end{cases} \begin{cases} 55.10 \text{ (d)} \\ 54.90 \text{ (d)}. \end{cases}$$
"

should read

--
$$\begin{cases} 70.11 \text{ (d)} \\ 69.21 \text{ (d)}. \end{cases} \begin{cases} 57.02 \text{ (q)}. \\ \end{cases} \begin{matrix} 56.60 \text{ (q)} \\ 57.43 \text{ (q)}. \end{matrix}$$
$$\begin{cases} 56.23 \text{ (q)} \\ 55.98 \text{ (q)}. \end{cases} \begin{cases} 56.72 \text{ (d)} \\ 52.91 \text{ (d)}. \end{cases} \begin{cases} 55.10 \text{ (d)} \\ 54.90 \text{ (d)}. \end{cases}$$
--;

line 41, "Layer Chromatorgraphy:" should read --Layer Chromatography:--;

line 49, "(12) Property of the Substance: neutral substance" delete in its entirety.

Column 26, line 47, "ULtraviolet" should read --Ultraviolet--;

line 50, "1450, 1830" should read --1450, 1380--.

UNITED STATES PATENT AND TRADEMARK OFFICE
CERTIFICATE OF CORRECTION

PATENT NO. : 5,254,562

DATED : OCTOBER 19, 1993

INVENTOR(S) : MASAKUNI OKUHARA et al

It is certified that error appears in the above-identified patent and that said Letters Patent is hereby corrected as shown below:

Column 26, lines 66-70,

"
$$\begin{Bmatrix} 73.89 \text{ (d)} \\ 73.70 \text{ (d)}. \end{Bmatrix} \quad \begin{Bmatrix} 73.70 \text{ (d)}. \\ \phantom{x} \end{Bmatrix} \quad \begin{matrix} 73.09 \text{ (d)} \\ 72.84 \text{ (d)}. \end{matrix}$$
$$70.40 \text{ (d)} \quad 56.75 \text{ (d)} \quad 56.93 \text{ (q)}$$
"

should read

--
$$\begin{Bmatrix} 73.89 \text{ (d)} \\ 73.70 \text{ (d)}. \end{Bmatrix} \quad 73.70 \text{ (d)}. \quad \begin{matrix} 73.09 \text{ (d)} \\ 72.84 \text{ (d)}. \end{matrix}$$
$$70.40 \text{ (d)} \quad 56.75 \text{ (d)} \quad 56.93 \text{ (q)}$$
--.

Column 27, lines 1-12

"
$$\begin{Bmatrix} 69.24 \text{ (d)}. \end{Bmatrix} \quad \begin{Bmatrix} 52.89 \text{ (d)}. \end{Bmatrix} \quad \begin{Bmatrix} 57.43 \text{ (q)}. \end{Bmatrix}$$
$$\begin{Bmatrix} 56.61 \text{ (q)} \\ 56.56 \text{ (q)}. \end{Bmatrix} \quad \begin{Bmatrix} 56.24 \text{ (q)} \\ 55.94 \text{ (q)}. \end{Bmatrix} \quad \begin{matrix} 48.58 \text{ (t)} \\ 48.32 \text{ (t)}. \end{matrix}$$
$$\begin{Bmatrix} 47.14 \text{ (d)} \\ 47.38 \text{ (d)}. \end{Bmatrix} \quad \begin{Bmatrix} 40.23 \text{ (d)} \\ 40.65 \text{ (d)}. \end{Bmatrix} \quad \begin{Bmatrix} 27.85 \text{ (t)} \\ 26.32 \text{ (t)}. \end{Bmatrix}$$
$$\begin{Bmatrix} 26.48 \text{ (d)} \\ 26.64 \text{ (d)}. \end{Bmatrix} \quad \begin{Bmatrix} 24.68 \text{ (t)}. \\ \phantom{x} \end{Bmatrix} \quad \begin{matrix} 21.33 \text{ (t)} \\ 20.83 \text{ (t)}. \end{matrix}$$
"

should read

--
$$\begin{Bmatrix} 69.24 \text{ (d)}. \end{Bmatrix} \quad \begin{Bmatrix} 52.89 \text{ (d)}. \end{Bmatrix} \quad \begin{Bmatrix} 57.43 \text{ (q)}. \end{Bmatrix}$$
$$\begin{Bmatrix} 56.61 \text{ (q)} \\ 56.56 \text{ (q)}. \end{Bmatrix} \quad \begin{Bmatrix} 56.24 \text{ (q)} \\ 55.94 \text{ (q)}. \end{Bmatrix} \quad \begin{matrix} 48.58 \text{ (t)} \\ 48.32 \text{ (t)}. \end{matrix}$$
$$\begin{Bmatrix} 47.14 \text{ (d)} \\ 47.38 \text{ (d)}. \end{Bmatrix} \quad \begin{Bmatrix} 40.23 \text{ (d)} \\ 40.65 \text{ (d)}. \end{Bmatrix} \quad \begin{Bmatrix} 27.85 \text{ (t)} \\ 26.32 \text{ (t)}. \end{Bmatrix}$$
$$\begin{Bmatrix} 26.48 \text{ (d)} \\ 26.64 \text{ (d)}. \end{Bmatrix} \quad 24.68 \text{ (t)}. \quad \begin{matrix} 21.33 \text{ (t)} \\ 20.83 \text{ (t)}. \end{matrix}$$
--.

UNITED STATES PATENT AND TRADEMARK OFFICE
CERTIFICATE OF CORRECTION

PATENT NO. : 5,254,562
DATED : OCTOBER 19, 1993
INVENTOR(S) : MASAKUNI OKUHARA et al

It is certified that error appears in the above-identified patent and that said Letters Patent is hereby corrected as shown below:

Column 27, lines 24-30,

"

| Stationary Phase | Developing Solvent | Rf Values |
|---|---|---|
| silica gel plate | chloroform :methanol (20:1. v/v) | 0.38 |
|  | ethyl acetate | 0.51 |
| (12) Property of the Substance: neutral substance | | |

"

should read --

| Stationary Phase | Developing Solvent | Rf Values |
|---|---|---|
| silica gel plate | chloroform :methanol (20:1. v/v) | 0.38 |
|  | ethyl acetate | 0.51 |

(12) Property of the Substance: neutral substance--.

Column 28, line 29, "like Preferable" should read --like. Preferable--.

Column 30, line 6, "salt thereof" should read --salt thereof.--;
line 18, "5 (3) Process" should read --(3) Process--.

Column 31, line 22, "(I±) or" should read --(Iℓ) or--.

UNITED STATES PATENT AND TRADEMARK OFFICE
CERTIFICATE OF CORRECTION

PATENT NO. : 5,254,562
DATED : OCTOBER 19, 1993
INVENTOR(S) : MASAKUNI OKUHARA et al

It is certified that error appears in the above-identified patent and that said Letters Patent is hereby corrected as shown below:

Column 31, line 44, "to (I$\pm$)" should read --to (I$\ell$)--.

Column 32, line 21, "3H-thymidine" should read --$^3$H-thymidine--.

Column 33, line 52, "ws defined" should read --was defined--.

Column 36, line 45, "measuring the both of ears" should read --measuring both of the ears--;
line 67, "test The mice" should read --test. The mice--.

Column 37, line 6, "control Twenty" should read --control. Twenty--;
line 13, "in Table 19" should read --in Table 19.--.

Column 38, line 58, "for 10 second" should read --for 10 seconds--.

UNITED STATES PATENT AND TRADEMARK OFFICE
CERTIFICATE OF CORRECTION

PATENT NO. : 5,254,562
DATED : OCTOBER 19, 1993
INVENTOR(S) : MASAKUNI OKUHARA et al

It is certified that error appears in the above-identified patent and that said Letters Patent is hereby corrected as shown below:

Column 39, line 35, "(2 liters) This" should read --(2 liters). This--;
line 36, "(2 liters) The" should read --(2 liters). The--;
line 41, "acetate After" should read --acetate. After--;
line 49, "oily residue The" should read --oily residue. The--;
line 62, "n-hexane Fractions" should read --n-hexane. Fractions--;
line 67, "100 mg Of this" should read --100 mg of this--.

Column 40, line 2, "as a carrier This" should read --as a carrier. This--;
line 6, "ml/minute., and" should read --ml/minute, and--;
line 40, "in advance After" should read --in advance. After--;
line 54, "residue The oily" should read --residue. The oily--.

UNITED STATES PATENT AND TRADEMARK OFFICE
CERTIFICATE OF CORRECTION

PATENT NO.  : 5,254,562
DATED       : OCTOBER 19, 1993
INVENTOR(S) : MASAKUNI OKUHARA et al

It is certified that error appears in the above-identified patent and that said Letters Patent is hereby corrected as shown below:

Column 40, line 60, "n-hexane The" should read --n-hexane. The--;
line 65, "residue The oily" should read --residue. The oily--.

Column 41, line 2, "n-hexane The" should read --n-hexane. The--;
line 8, "(1 1 v/v, 300 ml)" should read --1:1 v/v, 300 ml)--;
line 18, "reduced pressure This" should read --reduced pressure. The--;
line 63, "oily residue The" should --oily residue. The--.

Column 42, line 1, "n-hexane The" should read --n-hexane. The--;
line 19, "oily residue The" should read --oily residue. The--;
line 25, "with n-hexane Fractions" should read --with n-hexane. Fractions--;

UNITED STATES PATENT AND TRADEMARK OFFICE
CERTIFICATE OF CORRECTION

PATENT NO. : 5,254,562

DATED : OCTOBER 19, 1993

INVENTOR(S) : MASAKUNI OKUHARA et al

It is certified that error appears in the above-identified patent and that said Letters Patent is hereby corrected as shown below:

Column 42, line 29, "(380 mg) This" should read --(380 mg). This--;

line 57, "Petri dish The" should read --Petri dish. The--;

line 62, "could be found" should read --could be found.--.

Column 43, line 7, "(4 5%)" should read --(4.5%)--;

line 20, "the extract The" should read --the extract. The--;

line 28, "(4 liters) The" should read --(4 liters). The--;

line 30, "residue The oily" should read --residue. The oily--;

line 36, "with n-hexane The" should read --with n-hexane. The--;

line 41, "residue The oily" should read --residue. The oily--;

line 52, "(10 ml) This" should read --(10 ml). This--.

UNITED STATES PATENT AND TRADEMARK OFFICE
CERTIFICATE OF CORRECTION

PATENT NO. : 5,254,562

DATED : OCTOBER 19, 1993

INVENTOR(S) : MASAKUNI OKUHARA et al

It is certified that error appears in the above-identified patent and that said Letters Patent is hereby corrected as shown below:

Column 43, line 60, "powder This powder" should read --powder. This powder--;

line 61, "ether After" should read --ether. After--;

line 64, "pressure Recrystallization" should read --pressure. Recrystallization--.

Column 44, line 5, "powder This crude" should read --powder. This crude--;

line 13, "(190 mg) The" should read --(190 mg). The--;

line 18, "56mg of crystals Recrystallization" should read --56 mg of crystals. Recrystallization--;

line 19, "34mg" should read --34 mg--;

line 28, "pressure The residue" should read --pressure. The residue--;

line 33, "[22.3.1 .0$^{4,9}$]" should read --[22.3.1.0$^{4,9}$]--;

line 38, "(52 5 mg) in" should read --(52.5 mg) in--.

UNITED STATES PATENT AND TRADEMARK OFFICE
CERTIFICATE OF CORRECTION

PATENT NO. : 5,254,562
DATED : OCTOBER 19, 1993
INVENTOR(S) : MASAKUNI OKUHARA et al

It is certified that error appears in the above-identified patent and that said Letters Patent is hereby corrected as shown below:

Column 45, line 5, "(8   0mg)" should read --(8.0 mg)--;
     line 23, "methylvinyl-11," should read --methylvinyl]-11--;
     line 31, "methylvinyl-11," should read --methylvinyl]-11--;
     line 41, "(2-1   methyloxyacetoxy)" should read --(2-$\ell$ methyloxyacetoxy)--;
     line 43, "[22.3.1.0$^{4,9}$ octacos" should read --[22.3.1.0$^{4,9}$] octacos--;
     line 45, "(developing solvent" should read --(developing solvent:--.

Column 46, line 43, "pressure The residue" should read --pressure. The residue--;
     line 44, "(developing solvent diethyl" should read --(developing solvent: diethyl--;
     line 45, "dihydroxy-12-2-[4" should read --dihydroxy-12-[2-[4--;
     line 48, "[22.3.1.0$^{4,9}$   ]octacosa" should read --[22.3.1.0$^{4,9}$]octacosa--;
     line 68, "(2H, m)," should read --(2H, m)--.

UNITED STATES PATENT AND TRADEMARK OFFICE
CERTIFICATE OF CORRECTION

PATENT NO. : 5,254,562
DATED : OCTOBER 19, 1993
INVENTOR(S) : MASAKUNI OKUHARA et al

It is certified that error appears in the above-identified patent and that said Letters Patent is hereby corrected as shown below:

Column 47, line 24, "pressure The residue" should read --pressure. The reside--;

line 28, "dihydroxy-2 ,25" should read --dihydroxy-23,25--;

line 30, "16-t traone" should read --16-tetraone--;

line 49, "hours The reaction" should read --hours. The reaction--;

line 54, "pressure The residue" should read --pressure. The residue--;

line 59, "[22.3.1.04,9] should read --[22.3.1.0$^{4,9}$]--.

Column 48, line 16, "[22.3.1  9  octacos" should read --22.3.1.0$^{4,9}$]octacos--;

line 18, "(0.5 ml}" should read --(0.5ml)--;

line 28, "(26 5 mg)" should read --(26.5 mg)--.

Column 49, line 9, "chromatography Development" should read --chromatography. Development--.

UNITED STATES PATENT AND TRADEMARK OFFICE
CERTIFICATE OF CORRECTION

PATENT NO. : 5,254,562
DATED : OCTOBER 19, 1993
INVENTOR(S) : MASAKUNI OKUHARA et al

It is certified that error appears in the above-identified patent and that said Letters Patent is hereby corrected as shown below:

Column 49, line 13, "[22.3.1.04,9 octacos" should read --[22.3.1.0$^{4,9}$]octacos--;

line 32, "column Each" should read --column. Each--;

line 47, "acetate The solvent" should read --acetate. The solvent--.

Column 51, line 32, "ehtyl," should read --ethyl,--;

line 33, "1 to 2" should read --1 or 2--.

Column 56, line 22, "group consisting" should read --group consisting of--;

line 37, "claim 1-9 which" should read --claims 1-9 which--.

Signed and Sealed this

Twenty-first Day of March, 1995

Attest:

BRUCE LEHMAN

Attesting Officer

Commissioner of Patents and Trademarks